US012676210B2

(12) United States Patent
Fang et al.

(10) Patent No.: US 12,676,210 B2
(45) Date of Patent: Jul. 7, 2026

(54) GENE ALIGNMENT TECHNOLOGY

(71) Applicant: Huawei Technologies Co., Ltd.,
Shenzhen (CN)

(72) Inventors: Tao Fang, Hangzhou (CN); Xiajie Chen, Shenzhen (CN); Xiaowen Dong, Shenzhen (CN)

(73) Assignee: HUAWEI TECHNOLOGIES CO., LTD., Shenzhen (CN)

( * ) Notice: Subject to any disclaimer, the term of this patent is extended or adjusted under 35 U.S.C. 154(b) by 1190 days.

(21) Appl. No.: 17/587,507

(22) Filed: Jan. 28, 2022

(65) Prior Publication Data

US 2022/0238185 A1     Jul. 28, 2022

Related U.S. Application Data

(63) Continuation of application No. PCT/CN2020/106498, filed on Aug. 3, 2020.

(30) Foreign Application Priority Data

Aug. 2, 2019 (CN) .......................... 201910713689.5
Oct. 30, 2019 (CN) .......................... 201911046513.5

(51) Int. Cl.
*G16B 30/10* (2019.01)

(52) U.S. Cl.
CPC ................................... *G16B 30/10* (2019.02)

(58) Field of Classification Search
None
See application file for complete search history.

(56) References Cited

U.S. PATENT DOCUMENTS

| | | | |
|---|---|---|---|
| 2013/0091121 A1 | 4/2013 | Galinsky | |
| 2014/0309142 A1 | 10/2014 | Tian | |
| 2019/0170904 A1 | 6/2019 | Topolancik et al. | |

FOREIGN PATENT DOCUMENTS

| | | | |
|---|---|---|---|
| CN | 105039147 B | 5/2016 | |
| CN | 107653299 A | 2/2018 | |
| CN | 108604260 A | 9/2018 | |
| CN | 109690359 A | 4/2019 | |
| WO | 2017123664 A1 | 7/2017 | |

OTHER PUBLICATIONS

Kim, J.S., Senol Cali, D., Xin, H. et al. GRIM-Filter: Fast seed location filtering in DNA read mapping using processing-in-memory technologies. BMC Genomics 19 (Suppl 2), 89 (2018) (Year: 2018).*
Ehsan Maleki, Hossein Babashah, Somayyeh Koohi, and Zahra Kavehvash, "All-optical DNA variant discovery utilizing extended DV-curve-based wavelength modulation," J. Opt. Soc. Am. A 35, 1929-1940 (2018). (Year: 2018).*
Ehsan Maleki, Hossein Babashah, Somayyeh Koohi, and Zahra Kavehvash, "High-speed all-optical DNA local sequence alignment based on a three-dimensional artificial neural network," J. Opt. Soc. Am. A 34, 1173-1186 (2017) (Year: 2017).*
Maleki E, Koohi S, Kavehvash Z, Mashaghi A. OptCAM: An ultra-fast all-optical architecture for DNA variant discovery. J Biophotonics. Jan. 2020;13(1):e201900227. Epub Aug. 29, 2019. (Year: 2019).*
Akbari Rokn Abadi S, Hashemi Dijujin N, Koohi S (2021) Optical pattern generator for efficient bio-data encoding in a photonic sequence comparison architecture. PLOS ONE 16(1): e0245095. (Year: 2021).*
Millaray Curilem Saldías, et al., "Image Correlation Method for DNA Sequence Alignment," PLOS ONE, vol. 7, No. 6, Jun. 27, 2012, p. e39221, XP093280537, total 11 pages.
Fereshte Mozafari et al, DNA Sequence Alignment by Window based Optical Correlator, Oct. 3, 2017, 35 pages.
Masoome Fazelian et al, "Mining DNA Sequences Based on Spatially Coded Technique Using Spatial Light Modulator," Iran Workshop on Communication and Information Theory (IWCIT), 2016, 6 pages.
James K. Senter et al, "Unaligned Sequence Similarity Search Using Deep Learning," Sep. 16, 2019, 9 pages.
Brousseau N et al, "Analysis of DNA Sequences by an Optical Time-Integrating Correlator," Applied Optics, Optical Society of America, Washington, DC, US, vol. 31, No. 23, Aug. 10, 1992, pp. 4802-4815, XP000294341.
Fereshte Mozafari et al, "Speeding up DNA sequence alignment by optical correlator," Optics and Laser Technology, Elsevier Science Publishers BV., Amsterdam, NL, vol. 108, Jul. 11, 2018, pp. 124-135, XP085443749.

* cited by examiner

*Primary Examiner* — Kaitlyn L Minchella
*Assistant Examiner* — Jonathan Edward Hayes
(74) *Attorney, Agent, or Firm* — Conley Rose, P.C.

(57) ABSTRACT

A gene alignment technology may be applied to a computer system including an optical computing chip. In a process of performing gene alignment, a first group of gene fragments may be first obtained from a gene database based on a to-be-tested gene sequence, where the first group of gene fragments includes a plurality of reference gene fragments that match some bases of the to-be-tested gene sequence. After the first group of gene fragments is obtained, the to-be-tested gene sequence and the plurality of reference gene fragments in the first group of gene fragments may be input into the optical computing chip to perform optical alignment.

22 Claims, 14 Drawing Sheets

Specification includes a Sequence Listing.

Light source array
202

Modulator array
204

First concave mirror
208

Second concave mirror
210

Detector
array
206

Input A                Input B                Output C

First              First convex        Second          Second          Detector
modulator             lens            modulator      convex lens         310
302                  304               306             308

GENE ALIGNMENT TECHNOLOGY

CROSS-REFERENCE TO RELATED APPLICATIONS

This is a continuation of Int'l Patent App. No. PCT/CN2020/106498, filed on Aug. 3, 2020, which claims priority to Chinese Patent App. No. 201910713689.5, filed on Aug. 2, 2019, and Chinese Patent App. No. 201911046513.5, filed on Oct. 30, 2019, all of which are incorporated by reference.

REFERENCE TO A SEQUENCE LISTING

The content of the sequence listing submitted electronically via EFS-Web named "USSN 17-587507—Sequence Listing_ST25.txt" having a size of 2,352 bytes and created on Mar. 15, 2022 is incorporated herein by reference in its entirety.

FIELD

This disclosure relates to the field of optical technologies, and in particular, to a gene alignment technology.

BACKGROUND

Deoxyribonucleic acid (DNA) is a main chemical constituent of a chromosome and is also a material for making up a gene. The gene is a DNA sequence that carries genetic information, is also referred to as a genetic factor, and is a basic structural unit and functional unit of a genetic material that controls biological traits. The gene expresses, by guiding synthesis of proteins, the genetic information carries in the gene, to control trait performance of a biont. With advent of DNA sequencing technologies, until completion of the Human Genome Project (HGP), generation of DNA sequencing data shows exponential growth. DNA sequence alignment is a premise of gene recognition, information analysis, structure prediction, and the like. Same and different sites and regions are found through alignment of a plurality of DNA sequences, to help determine homology, variation points, and sources of to-be-tested genes.

With rapid development of next-generation DNA sequencing technologies, an explosive accumulation speed of the DNA sequencing data is much faster than a processing speed of the DNA sequencing data. To resolve these big data analysis tasks and data integration in different dimensions in the bioinformatics field, a fast and convenient DNA alignment method is urgently needed.

SUMMARY

This disclosure provides a gene alignment technology, to increase DNA alignment efficiency.

According to a first aspect, an embodiment provides a gene alignment method. The method is applied to a computer system including an optical computing chip. According to the method, in a process of implementing gene alignment, a processor of the computer system may obtain a first group of gene fragments from a gene database based on a to-be-tested gene sequence, and input the to-be-tested gene sequence and a plurality of reference gene fragments in the first group of gene fragments into the optical computing chip to perform optical alignment. The gene database includes a plurality of reference gene fragments of a reference gene sequence, and the first group of gene fragments includes a plurality of reference gene fragments that match some bases of the to-be-tested gene sequence.

According to the gene alignment method provided in this embodiment, two manners, namely, database search and optical autocorrelation alignment, are combined, and initial matching is performed on the to-be-tested gene sequence by using the constructed gene database, to screen out the first group of reference gene fragments that may match the to-be-tested gene sequence. After to-be-aligned gene fragments are screened by using the gene database provided in this embodiment, a quantity of reference gene fragments that need to be thoroughly aligned can be greatly reduced. In addition, in this embodiment, after the first group of reference gene fragments is obtained, optical alignment is further performed between the to-be-tested gene sequence and the plurality of reference gene fragments in the first group of reference gene fragments by using the optical computing chip. An alignment speed of optical alignment performed by the optical computing chip is faster than an alignment speed of a method of electrical gene alignment. Therefore, the gene alignment method provided in this embodiment also greatly increases alignment efficiency.

The processor may obtain the first group of gene fragments from the database based on the some bases of the to-be-tested gene sequence. For example, the first group of gene fragments is obtained from the database based on the first m bases and the last n bases of the to-be-tested gene sequence, where both a value of m and a value of n are greater than 0, and a sum of m and n is less than a quantity of bases in the to-be-tested gene sequence. Generally, the values of m and n may be determined based on factors such as a length of the to-be-tested gene sequence and a length of the reference gene sequence.

In a possible implementation, the database may be a key-value database, where key indicates some bases of the plurality of reference gene fragments in the reference gene sequence. The values indicate locations of the plurality of reference gene fragments in the reference gene sequence.

In a possible implementation, the method further includes: when determining, based on an output result of the optical computing chip, that a similarity degree between the to-be-tested gene sequence and a first gene fragment in the first group of gene fragments is less than a first threshold and greater than a second threshold, obtaining a plurality of reference gene subsequences from the reference gene sequence; and inputting the to-be-tested gene sequence and a first reference gene subsequence in the plurality of reference gene subsequences into the optical computing chip to perform optical alignment, to obtain a first similarity degree between the to-be-tested gene sequence and the first reference gene subsequence, where each reference gene subsequence is a part of the reference gene sequence.

In this embodiment, when a similarity degree between the to-be-tested gene sequence and at least one gene fragment in the first group of gene fragments is less than the first threshold and greater than the second threshold, it indicates that a matched reference gene fragment is likely to be found for the to-be-tested gene sequence in the reference gene sequence. Further alignment may be required. Therefore, optical alignment may be further performed between the to-be-tested gene sequence and the plurality of reference gene subsequences of the reference gene sequence, so that a reference gene segment that matches at least some segments of the to-be-tested gene sequence can be quickly found.

In another possible implementation, the method may further include: determining that the first similarity degree is greater than a third threshold and less than a fourth threshold; and in response to the determining, obtaining a first to-be-tested gene subsequence and a second to-be-tested gene subsequence based on the to-be-tested gene sequence, where the fourth threshold is not greater than the first threshold, and some bases of the first to-be-tested gene subsequence are the same as some bases of the second to-be-tested gene subsequence. Further, the first to-be-tested gene subsequence and the first reference gene subsequence are input into the optical computing chip to perform optical alignment, to obtain a second similarity degree; and the second to-be-tested gene subsequence and the first reference gene subsequence are input into the optical computing chip to perform optical alignment, to obtain a third similarity degree. In this manner, when the similarity degree between the to-be-tested gene sequence and the first reference gene subsequence meets a preset condition, the to-be-tested gene sequence may be further split. The first to-be-tested gene subsequence and the second to-be-tested gene subsequence that are obtained after splitting are separately aligned with the first reference gene subsequence, so that some segments that are of the to-be-tested gene sequence and that match the first reference gene subsequence can be located as soon as possible. Moreover, because this maximum similarity matching method can allow base deletion, a deletion part or a variant part in the to-be-tested gene sequence can be exactly located. The first to-be-tested gene subsequence may include bases of a first preset length obtained from a head-to-tail direction of the to-be-tested gene sequence. The second to-be-tested gene subsequence may include bases of the first preset length obtained from a tail-to-head direction of the to-be-tested gene sequence. The some bases of the first to-be-tested gene subsequence overlap with the some bases of the second to-be-tested gene subsequence.

In still another possible implementation, the method further includes: when the second similarity degree is greater than the fourth threshold, recording a location of the first reference gene subsequence in the reference gene sequence. In this manner, when the second similarity degree between the first to-be-tested gene subsequence and the first reference gene subsequence is greater than the fourth threshold, it may be determined that the first to-be-tested gene subsequence matches the first reference gene subsequence at a maximum similarity degree. In this way, the location of the first reference gene subsequence in the reference gene sequence can be recorded, and a segment that matches the first to-be-tested gene subsequence at a maximum similarity degree is obtained.

In still another possible implementation, the method further includes: when the third similarity degree is greater than the third threshold and less than the fourth threshold, obtaining a first to-be-tested gene subsequence unit and a second to-be-tested gene subsequence unit based on the second to-be-tested gene subsequence; inputting the first to-be-tested gene subsequence unit and the first reference gene subsequence into the optical computing chip to perform optical alignment; and inputting the second to-be-tested gene subsequence unit and the first reference gene subsequence into the optical computing chip to perform optical alignment. Some bases of the first to-be-tested gene subsequence unit are the same as some bases of the second to-be-tested gene subsequence unit. In this manner, if a matching result between the second to-be-tested gene subsequence and the first reference gene subsequence still does not reach a maximum similarity matching criterion, splitting and alignment may continue to be performed on the second to-be-tested gene subsequence. Therefore, based on this recursive searching manner, a fragment that matches at least some fragments of the second to-be-tested gene sequence at a maximum similarity degree can be quickly located. Because this maximum similarity matching method can allow base deletion, a gene deletion point and a genovariation point can be exactly located.

In still another possible implementation, the method further includes: inputting the to-be-tested gene sequence and a second reference gene subsequence in the plurality of reference gene subsequences into the optical computing chip to perform optical alignment, to obtain a fourth similarity degree between the to-be-tested gene sequence and the second reference gene subsequence; and inputting the to-be-tested gene sequence and a third reference gene subsequence in the plurality of reference gene subsequences into the optical computing chip to perform optical alignment, to obtain a fifth similarity degree between the to-be-tested gene sequence and the third reference gene subsequence, where the third reference gene subsequence is a reference gene subsequence immediately adjacent to the second reference gene subsequence. When it is determined that a sum of the fourth similarity degree and the fifth similarity degree is greater than the first threshold, a fourth reference gene subsequence is obtained based on the second reference gene subsequence and the third reference gene subsequence, and the to-be-tested gene sequence and the fourth reference gene subsequence are input into the optical computing chip to perform optical alignment. The fourth reference gene subsequence includes some bases of the second reference gene subsequence and some bases of the third reference gene subsequence.

In this manner, when it is determined that a value of the similarity degree between the to-be-tested gene sequence and the second reference gene subsequence does not meet a condition for further matching with the second reference gene subsequence, and the sum of the similarity degree between the to-be-tested gene sequence and the second reference gene subsequence and the similarity degree between the to-be-tested gene sequence and the third reference gene subsequence is greater than the first threshold, a location of the reference gene subsequence may be adjusted in time. The fourth reference gene subsequence is obtained by obtaining continuous parts from the second reference gene subsequence and the third reference gene subsequence, so that a segment that matches the to-be-tested gene sequence at a maximum similarity degree can be found from the fourth reference gene subsequence as soon as possible, and the to-be-tested gene fragment does not need to be further aligned with a reference gene subsequence following the third reference gene subsequence. In this manner of adjusting the reference gene subsequence in time based on a partial alignment result, a probability and a speed of obtaining a maximum similarity gene segment can be increased, and a quantity of alignment times can be reduced.

Some reference gene fragments may be separately obtained from the second reference gene subsequence and the third reference gene subsequence based on a ratio of the fourth similarity degree to the fifth similarity degree to constitute the fourth reference gene subsequence.

In still another possible implementation, the method further includes: determining, based on an output result of the optical computing chip, that a second gene fragment in the first group of gene fragments matches the to-be-tested gene sequence; and recording a location of the second gene fragment in the reference gene sequence.

In still another possible implementation, the inputting the to-be-tested gene sequence and a plurality of reference gene fragments in the first group of gene fragments into the optical computing chip to perform optical alignment includes: separately performing optical encoding on the to-be-tested gene sequence and the plurality of reference gene fragments in the first group of gene fragments; and separately inputting optical code of the to-be-tested gene sequence and optical code of the plurality of gene fragments in the first group of gene sequences into the optical computing chip to perform optical alignment. Optical encoding may be performed on the to-be-tested gene sequence and the plurality of reference gene fragments based on light intensity information and/or light spatial information.

According to a second aspect, an embodiment provides a gene alignment apparatus, including a processor and an optical computing chip. The processor is configured to obtain a first group of gene fragments from a database based on a to-be-tested gene sequence, where the database system includes a plurality of reference gene fragments of a reference gene sequence, and the first group of gene fragments includes a plurality of reference gene fragments that match some bases of the to-be-tested gene sequence. The optical computing chip is connected to the processor and configured to perform optical alignment between the to-be-tested gene sequence and the plurality of reference gene fragments in the first group of gene fragments.

In a possible implementation, the processor may obtain the first group of gene fragments from the database based on the some bases of the to-be-tested gene sequence. For example, the first group of gene fragments is obtained from the database based on the first m bases and the last n bases of the to-be-tested gene sequence, where both a value of m and a value of n are greater than 0, and a sum of m and n is less than a quantity of bases in the to-be-tested gene sequence. Specifically, the database may be a key-value database, where key indicates some bases of the plurality of reference gene fragments in the reference gene sequence, and values indicate locations of the plurality of reference gene fragments in the reference gene sequence.

In a possible implementation, the processor is further configured to: determine, based on an output result of the optical computing chip, that a similarity degree between the to-be-tested gene sequence and a first gene fragment in the first group of gene fragments is less than a first threshold and greater than a second threshold; and obtain a plurality of reference gene subsequences from the reference gene sequence, where each reference gene subsequence is a part of the reference gene sequence. The optical computing chip is further configured to perform optical alignment between the to-be-tested gene sequence and a first reference gene subsequence in the plurality of reference gene subsequences, to obtain a first similarity degree between the to-be-tested gene sequence and the first reference gene subsequence.

In another possible implementation, the processor is further configured to: determine that the first similarity degree is greater than a third threshold and less than a fourth threshold, where the fourth threshold is not greater than the first threshold; and in respond to the determining, obtain a first to-be-tested gene subsequence and a second to-be-tested gene subsequence based on the to-be-tested gene sequence, where some bases of the first to-be-tested gene subsequence are the same as some bases of the second to-be-tested gene subsequence. The optical computing chip is further configured to: perform optical alignment between the first to-be-tested gene subsequence and the first reference gene subsequence to obtain a second similarity degree; and perform optical alignment between the second to-be-tested gene subsequence and the first reference gene subsequence to obtain a third similarity degree.

In still another possible implementation, the processor is further configured to: when the second similarity degree is greater than the fourth threshold, record a location of the first reference gene subsequence in the reference gene sequence.

In still another possible implementation, the processor is further configured to: when the third similarity degree is greater than the third threshold and less than the fourth threshold, obtain a first to-be-tested gene subsequence unit and a second to-be-tested gene subsequence unit based on the second to-be-tested gene subsequence, where some bases of the first to-be-tested gene subsequence unit are the same as some bases of the second to-be-tested gene subsequence unit. The optical computing chip is further configured to perform optical alignment between the first to-be-tested gene subsequence unit and the first reference gene subsequence; and perform optical alignment between the second to-be-tested gene subsequence unit and the first reference gene subsequence.

In still another possible implementation, the optical computing chip is further configured to: perform optical alignment between the to-be-tested gene sequence and a second reference gene subsequence in the plurality of reference gene subsequences; and perform optical alignment between the to-be-tested gene sequence and a third reference gene subsequence in the plurality of reference gene subsequences, where the third reference gene subsequence is a reference gene subsequence immediately adjacent to the second reference gene subsequence. The processor is further configured to determine that a sum of a fourth similarity degree between the to-be-tested gene sequence and the second reference gene subsequence and a fifth similarity degree between the to-be-tested gene sequence and the third reference gene subsequence is greater than the first threshold; obtain a fourth reference gene subsequence based on the second reference gene subsequence and the third reference gene subsequence; and input the to-be-tested gene sequence and the fourth reference gene subsequence into the optical computing chip to perform optical alignment, where the fourth reference gene subsequence includes some bases of the second reference gene subsequence and some bases of the third reference gene subsequence.

In still another possible implementation, the processor is further configured to: determine, based on an output result of the optical computing chip, that a second gene fragment in the first group of gene fragments matches the to-be-tested gene sequence; and record a location of the second gene fragment in the reference gene sequence.

In still another possible implementation, the processor is further configured to: separately perform optical encoding on the to-be-tested gene sequence and the plurality of reference gene fragments in the first group of gene fragments; and separately input optical code of the to-be-tested gene sequence and optical code of the plurality of gene fragments in the first group of gene sequences into the optical computing chip to perform optical alignment.

According to a third aspect, an embodiment provides an alignment apparatus, including a processor and an optical computing chip. The processor is configured to obtain a first group of reference objects from a database based on a to-be-matched first object, where the first group of reference objects includes a plurality of reference objects whose some features are the same as some features of the first object. The optical computing chip is connected to the processor and configured to perform optical alignment between the first object and the plurality of reference objects.

According to the alignment apparatus provided in this embodiment, two manners, namely, database search and optical alignment, are combined. After to-be-aligned reference objects are screened by using the database, a quantity of reference objects that need to be thoroughly aligned can be greatly reduced. In addition, an alignment speed can be greatly increased by using the optical computing chip for alignment. The alignment apparatus provided in this embodiment can be applied not only to a gene testing scenario, but also to various scenarios in which massive data needs to be aligned.

In a possible implementation, the processor is further configured to: determine, based on an output result of the optical computing chip, that a similarity degree between the first object and a first reference object in the first group of reference objects is less than a first threshold and greater than a second threshold; and obtain a plurality of reference sub-objects based on a standard object, where each reference sub-object is a part of the reference object. The optical computing chip is further configured to perform optical alignment between the first object and a first reference sub-object in the plurality of reference sub-objects, to obtain a first similarity degree between the first object and the first reference sub-object.

In another possible implementation, the processor is further configured to: determine that the first similarity degree is greater than a third threshold and less than a fourth threshold; and in response to the determining, obtain a first sub-object and a second sub-object based on the first object, where the fourth threshold is not greater than the first threshold, and some data of the first sub-object is the same as some data of the second sub-object. The optical computing chip is further configured to perform optical alignment between the first sub-object and the first reference sub-object to obtain a second similarity degree; and perform optical alignment between the second sub-object and the first reference sub-object to obtain a third similarity degree.

In still another possible implementation, the processor is further configured to: when the second similarity degree is greater than the fourth threshold, record a location of the first reference sub-object in the standard object.

According to a fourth aspect, an alignment apparatus includes functional modules configured to implement the gene alignment method in any one of the first aspect or the possible implementations of the first aspect, such as an obtaining module, an alignment module, a result processing module, and a determining module.

According to a fifth aspect, a computer program product includes program code, where instructions included in the program code are executed by a computer, to implement the gene alignment method in any one of the first aspect and the possible implementations of the first aspect.

According to a sixth aspect, a computer-readable storage medium is configured to store program code, and instructions included in the program code are executed by a computer, to implement the gene alignment method in any one of the first aspect and the possible implementations of the first aspect.

BRIEF DESCRIPTION OF THE DRAWINGS

To describe technical solutions in embodiments of the present disclosure or in the conventional technology more clearly, the following briefly describes accompanying drawings used in describing the embodiments. Definitely, the accompanying drawings in the following descriptions show merely some embodiments.

DETAILED DESCRIPTION

To make a person skilled in the art understand solutions in the present disclosure better, the following clearly describes technical solutions with reference to accompanying drawings in the embodiments. Definitely, the described embodiments are merely some and other embodiments are possible.

As mentioned above, DNA sequencing data has explosively increased due to rapid development of DNA sequencing technologies. Therefore, how to increase a DNA alignment speed is a technical problem that urgently needs to be resolved. In the conventional technology, a search rate is usually accelerated by constructing an index for a reference gene sequence in a computer system. Essence of the index is to increase search efficiency by optimizing a data structure. However, there is a bottleneck in index optimization, and it takes lots of time to simultaneously create a plurality of responsible indexes. Therefore, efficiency of this gene alignment method is difficult to withstand a large increase in the DNA sequencing data. A gene alignment solution provided in the embodiments can greatly increase a gene alignment speed, and gene alignment can be quickly implemented even when massive gene sequencing data being processed.

To better understand the solution, several technical terms in the embodiments are first described.

A gene refers to genetic information that controls biological traits, and is usually carried by a DNA sequence. The gene may also be considered as a basic genetic unit, namely, a functional DNA or ribonucleic acid (RNA) sequence. A process of figuring out the sequence of the gene is referred to as gene sequencing.

A to-be-tested gene sequence may also be referred to as reads, is a small sequencing fragment, and is sequencing data generated by a high-throughput sequencing platform. In a process of sequencing an entire genome, hundreds of millions of reads are generated, and then the reads are spliced together to obtain a complete sequence of the genome.

A reference gene sequence (which may also be referred to as a reference sequence) is a standard sequence that has been verified and edited. The reference gene sequence can provide a basis for a functional annotation of a human genome. The reference gene sequence provides a stable reference point for mutation analysis, gene expression study, and polymorphism discovery. It should be noticed that, a person skilled in the art can easily understand that the reference gene sequence is also referred to as a gene fragment.

A base pair is a chemical structure for forming DNA and RNA monomers and encoding genetic information. Bases included in base pairs include adenine A, guanine G, thymine T, cytosine C, and uracil U. Strictly speaking, the base pair is a pair of matched bases (namely, A-T, G-C, A-U interactions) connected by hydrogen bonds. The base pair is often used to measure lengths of DNA and RNA (although the RNA is single-stranded).

Figure 1:
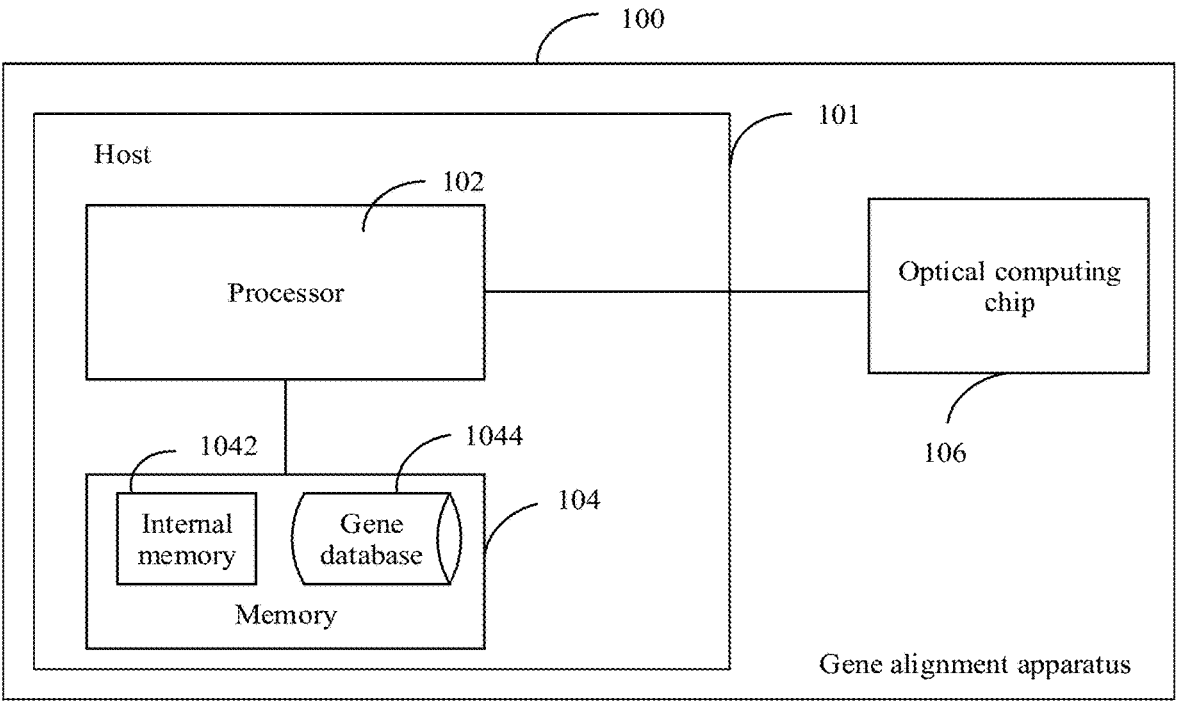
FIG. 1 is a schematic structural diagram of a gene alignment apparatus according to an embodiment.

The following describes the embodiments in detail. FIG. 1 is a schematic diagram of implementing gene alignment by using an optical system according to an embodiment. As shown in the figure, a gene alignment apparatus 100 may include a processor 102, a memory 104, and an optical computing chip 106. The processor 102 and the memory 104 may be considered as a part of a host 101. The optical computing chip 106 may be connected to the host 101 through a host interface. The host interface may include a standard host interface and a network interface. For example, the host interface may include a Peripheral Component Interconnect Express (PCIe) interface. Data may be sent to the optical computing chip 106 through the host interface, or data processed by the optical computing chip 106 may be sent to the processor 102 through the host interface. Alternatively, the processor 102 may monitor a working state of the optical computing chip 106 through the host interface. The processor 102 and the memory 104 may alternatively not be used as the part of the host, and the processor 102, the memory 104, and the optical computing chip 106 may be a part of a system on a chip (SoC).

The processor 102 is an operation core and a control core of the gene alignment apparatus 100. The processor 102 may include a plurality of processor cores. The processor 102 may be a hyperscale integrated circuit. An operating system and another software program are installed in the processor 102, so that the processor 102 can access an internal memory 1042, a cache, a magnetic disk, and a peripheral device (for example, the optical computing chip 106 in FIG. 1). It may be understood that, in this embodiment, the core in the processor 102 may be, for example, a central processing unit (CPU), a graphics processing unit (GPU), or a field-programmable gate array (FPGA); or may be another application-specific integrated circuit (ASIC), or the like.

The memory 104 is configured to store data. The memory 104 may include other memories that store data, such as the internal memory 1042 and the magnetic disk. The internal memory 1042 is a main memory of the host 101. The internal memory 1042 may be connected to the processor 102 through a double data rate (DDR) bus. The internal memory 1042 is usually configured to store various running software in the operating system; input and output data, information exchanged with an external memory, and the like. To increase an access speed of the processor 102, the internal memory 1042 needs to have an advantage of a fast access speed. A dynamic random-access memory (DRAM) may be used as the internal memory 1042. The processor 102 can access the internal memory 1042 at a high speed by using a memory controller (not shown in FIG. 1), and perform a read operation and a write operation on any storage unit in the internal memory 1042.

In this embodiment, the memory 104 may be configured to store a gene database 1044. The gene database 1044 may be a key-value database established based on a reference sequence, where key may be obtained based on some bases of a gene fragment, and values may include a location of a reference gene segment corresponding to key in the memory, and may further include a location of the reference gene segment corresponding to key in the reference gene sequence.

Figure 2A:
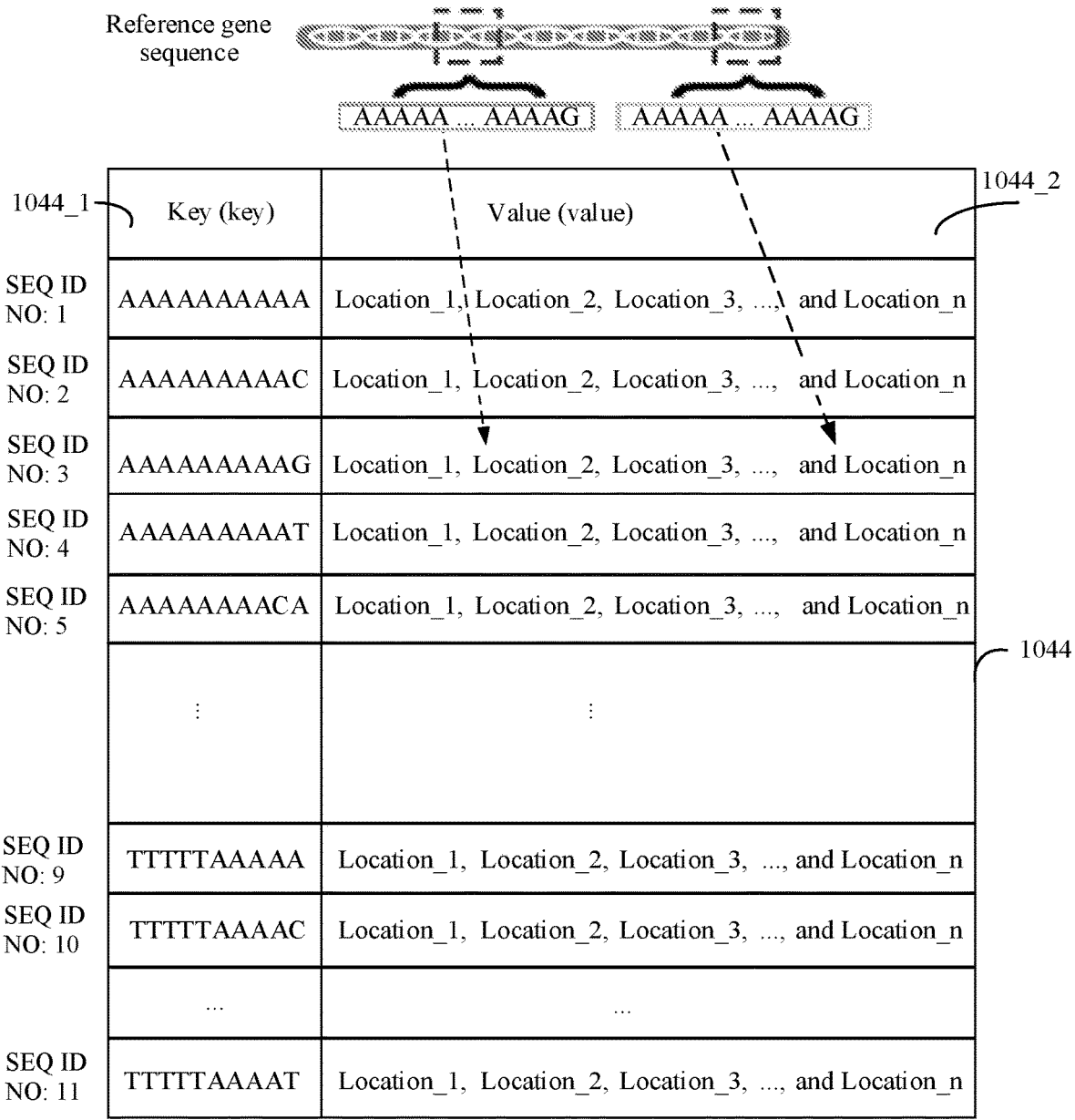
FIG. 2A is a schematic diagram of a gene database according to an embodiment.
Figures 2B, 3A:
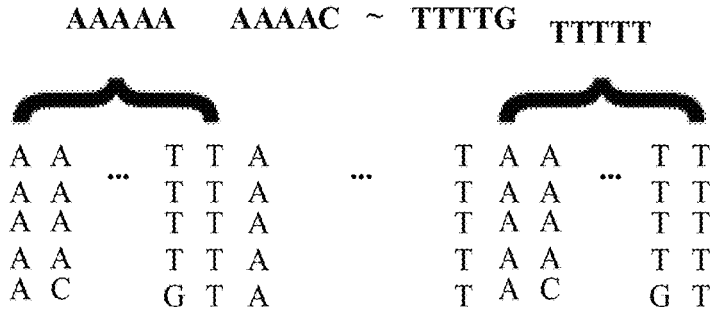
FIG. 2B is a schematic diagram of optical encoding according to an embodiment.
FIG. 3A is a schematic structural diagram of an optical computing chip according to an embodiment.

In this embodiment, some bases of the reference gene sequence may be used as key, for example, the first m bases and the last n bases of a reference gene fragment of a preset length may be used as key, where m and n may be the same or different. This is not limited herein. The reference gene sequence is traversed to locate all reference gene fragments that meet key, and location information of all of the reference gene fragments is recorded as values corresponding to key. FIG. 2A is a schematic diagram of a gene database according to an embodiment. As shown in FIG. 2A, the gene database 1044 may include key 1044_1 and value 1044_2. 10 bases are used as an example in key 1044_1 part. Specifically, five bases at the head of a reference segment and five bases at the tail of the reference segment may be separately taken as key. In this embodiment, how to establish the gene database 1044 is described by using an example in which 150 bases are a length of the reference gene fragment. Specifically, an index table (with only keys) of an empty set is first constructed, where a quantity of rows of the index table is $4^{5+5}$, and a sorting combination of keys is alphabetical sorting from SEQ ID NO: 1 (AAAAAAAAAA) to SEQ ID NO: 12 (TTTTTTTTTT). A mapping manner is shown in FIG. 2B. Specifically, bases at the head are arranged in a high order and bases at the tail are arranged in a low order. Bases at a same order are advanced in an order of A, C, G, and T. When a base at the low order is T, a base that is before the base at the low order and has an order higher than the base at the low order becomes C. When the bases at the tail are all TTTTT, the fifth base at the head changes C from A. In this manner, the following order of bases can be obtained: SEQ ID NO: 1 (AAAAAAAAAA), SEQ ID NO: 2 (AAAAAAAAAC), SEQ ID NO: 3 (AAAAAAAAAG), SEQ ID NO: 4 (AAAAAAAAAT), SEQ ID NO: 5 (AAAAAAAACA), SEQ ID NO: 6 (AAAAAAAACC), SEQ ID NO: 7 (AAAAAAAACG), SEQ ID NO: 8 (AAAAAAAACT), and the like. Thus, key 1044_1 shown in FIG. 2A can be obtained.

After the key-value index table is established, a preset base length is successively used as a unit window, and a step length is used as a unit base (namely, one base) to slide on a reference gene sequence, to obtain a plurality of reference gene fragments. In a process of obtaining each reference gene fragment, key of the reference gene fragment may be obtained based on five bases at the head of the reference gene fragment and five bases at the tail of the reference gene fragment. A location of the reference gene fragment in the reference gene sequence is recorded in value 1044_2 corresponding to key. For example, a location of the first base of the reference gene fragment may be recorded. In this manner, after sliding to the end of the reference gene sequence, values of all reference gene fragments (namely, location information of the reference gene fragments) of the reference gene sequence are obtained. Thus, the gene database 1044 as shown in FIG. 2A can be established.

The mapping manner of key depends on a permutation and combination form. It is assumed that sequence fragments of the first n bases and the last m bases are respectively $Seq_1$ and $Seq_2$, and mapping of key is defined as:

$$Key_{mapping} = \left( \sum_{i=1}^{n} Seq_1[i-1] \times 4^{i-1} \right) \times 4^n + \sum_{j=1}^{m} Seq_2[j-1] \times 4^{j-1}$$

For example, if a DNA sequence is GTGGA . . . CGAGC, and it is assumed that values of A, C, G, and T are respectively 0, 1, 2, and 3, key corresponding to the sequence is as follows:

$$Key_{GTG...AGC} =$$
$$\left( Seq_1[4] \times 4^4 + Seq_1[3] \times 4^3 + Seq_1[2] \times 4^2 + Seq_1[1] \times 4^1 + Seq_1[0] \times 4^0 \right) \times$$
$$4^5 + Seq_2[4] \times 4^4 + Seq_2[3] \times 4^3 + Seq_2[2] \times 4^2 +$$
$$Seq_2[1] \times 4^1 + Seq_2[0] \times 4^0 = 728 \times 4^5 + 393 = 745865$$

It may be understood that selection of quantities of n and m bases directly affect efficiency of an algorithm, and increases of n and m cause a decrease in values (namely, location information) stored in key. If a hardware factor is not considered, an addressing rate for each to-be-tested gene sequence is increased of four times by each time one base is increased. However, because a sequencing error and a genetic mutation limit infinite increases of n and m, increasing n and m may decrease reliability of key. Therefore, values of m and n may be determined based on a requirement, and the length of the reference gene fragment may also be set based on an actual requirement. Generally, the values of m and n may be determined based on factors such as a length of the to-be-tested gene sequence and a length of the reference gene sequence. The length of the reference gene fragment is usually the same as a base length of the to-be-tested gene sequence.

The optical computing chip 106 may be an on-chip optical computing system. FIG. 3A is a schematic structural diagram of an optical computing chip according to an embodiment. As shown in FIG. 3A, the optical computing chip 106 may include a light source array 202, a modulator array 204, a detector array 206, a first concave mirror 208, and a second concave mirror 210. The light source array 202 is located on an objective focal plane of the first concave mirror 208, the modulator array 204 is located on an image focal plane of the first concave mirror 208, and the modulator array 204 is also located on an objective focal plane of the second concave mirror 210. The detector array 206 is located on an image focal plane of the second concave mirror 210.

The light source array 202 is configured to modulate and transmit data as a data input unit of the optical computing chip 106. The light source array 202 may generate a plurality of optical signals of different light intensities based on input data. The first concave mirror 208 is configured to implement standard Fourier transform on the optical signals data sent by the light source array 202. The modulator array 204 has two working modes: a recording mode and a modulation mode. The recording mode is used to obtain an image of a spectral plane after the optical signals data sent by the light source array 202 pass through the first concave mirror 208. The modulation mode is used to modulate, on the modulator array 204, the image of the spectral plane after the optical signals data sent by the light source array 202 pass through the first concave mirror 208. The second concave mirror 210 is configured to implement standard inverse Fourier transform on optical signals that pass through the modulator array 204. The detector array 206 is used for light intensity signal detection as a result output unit of the optical computing chip 106.

Figure 3B:
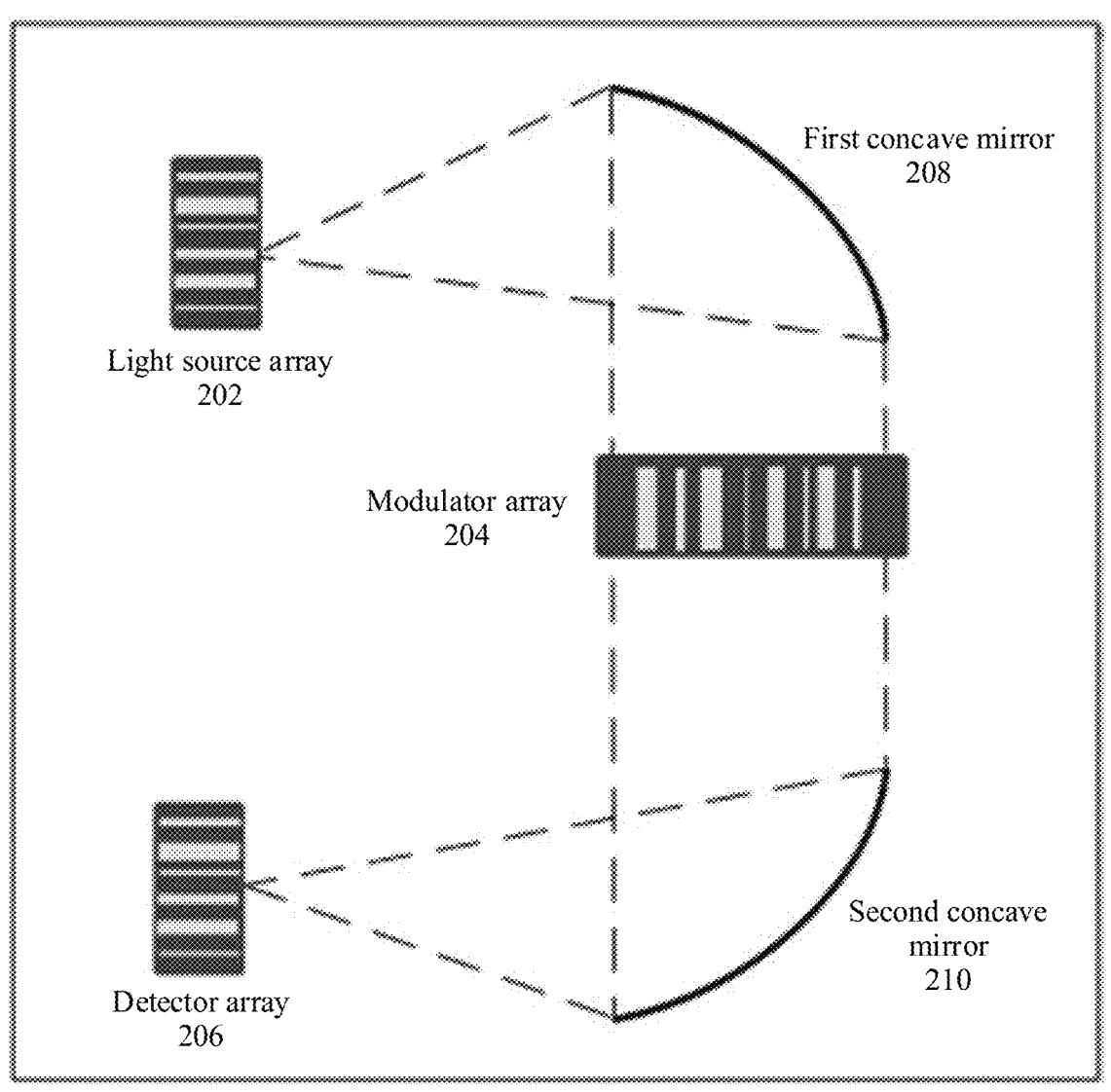
FIG. 3B is a schematic structural diagram of another optical computing chip according to an embodiment.

FIG. 3B is a schematic structural diagram of still another optical computing chip according to an embodiment. Different from the optical computing chip provided in FIG. 3A, in the optical computing chip shown in FIG. 3B, the light source array 202 and the detector array 206 are disposed on a same side of the chip, so that a structure of the entire computing chip is more compact, and a chip size can be reduced. As shown in FIG. 3B, compared with the optical computing chip shown in FIG. 3A, locations of the first concave mirror 208, the second concave mirror 210, and the modulator array 204 remain unchanged; and focal length locations of the light source array 202, the modulator array 204, and the detector array 206 with respect to the first concave mirror 208 and the second concave mirror 210 also remain unchanged. For implementation of each component shown in FIG. 3B, refer to descriptions of each component in the optical computing chip shown in FIG. 3A. Details are not described herein again.

Figure 3C:
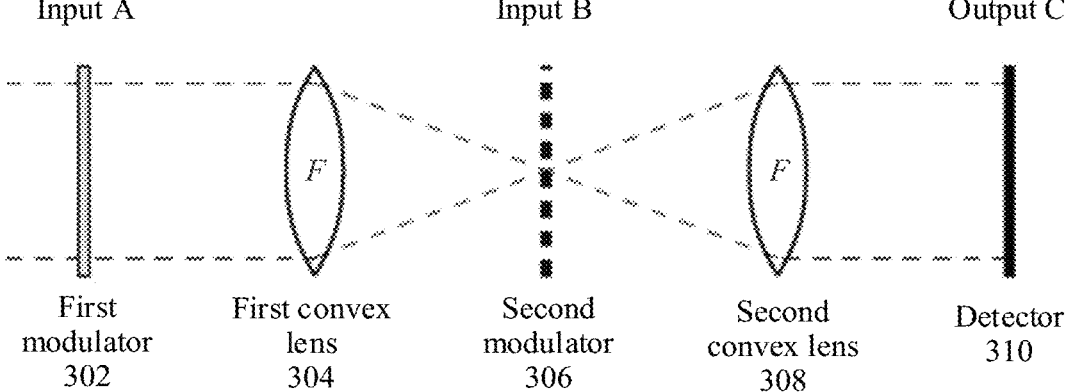
FIG. 3C is a schematic diagram of a principle of optical alignment according to an embodiment.

FIG. 3A and FIG. 3B are merely schematic structural diagrams of the optical computing chip according to the embodiments. A specific structure of the optical computing chip 106 is not limited, and an optical computing chip of another structure may alternatively be used. For example, the optical computing chip 106 may alternatively be an optical computing chip of another structure implemented by using a principle of a 4F optical computing system. FIG. 3C is a schematic diagram of the principle of the 4F optical computing system. As shown in FIG. 3C, a first modulator 302 is located at an object plane focus location of a first convex lens 304. A second modulator 306 is located at an image plane focus location of the first convex lens 304, and is located at an object plane focus location of a second convex lens 308. A spacing between the first convex lens 304 and the second convex lens 308 is a sum of focal lengths of the two convex lenses (304 and 308). A detector 310 is located at an image plane focus location of the second convex lens 308, and a length of the entire system is four times the focal length. When data alignment is performed by using the 4F optical computing system shown in FIG. 3C, to-be-aligned first data may be loaded onto the first modulator 302, and reversed spectrum data of second data may be loaded onto the second modulator 306. Therefore, after an optical signal generated based on the to-be-aligned first data passes through the first convex lens 304, Fourier transform is performed on the optical signal at a location of the second modulator 306 to convert the optical signal into a spectrum optical signal, and a multiplication operation is completed with the reversed spectrum data of the second data on the second modulator 306 in optical space. Optical field energy distribution of the s spectrum optical signal of to-be-aligned the first data in the optical space is essentially changed. A multiplied spectrum optical signal undergoes inverse Fourier transform through the second convex lens 308, and then returns to a time domain optical signal. The detector 310 may obtain an autocorrelation result of the two pieces of data by detecting an intensity of the time domain optical signal that passes through the second convex lens 308. It should be noted that both the first data and the second data loaded onto the optical computing chip may be vectors.

It may be understood that a process in which the optical computing chip in FIG. 3A to FIG. 3C implements data alignment is obtained by detecting an autocorrelation result of optical signals of two pieces of data in optical space. A person skilled in the art may know that autocorrelation is also referred to as sequence correlation, and is a cross-correlation of a signal with a delayed copy of itself as a function of delay. To put it another way, autocorrelation is the similarity between observations as a function of the time lag between them. Autocorrelation is a mathematical tool for finding repeating patterns of sequences of random variables. In actual sequence recognition, an autocorrelation operation can be used to ensure that when a to-be-tested sequence and a target sequence are the same, an autocorrelation result of the sequences appears at an obvious location with a maximum value, and sequence alignment can be easily realized by monitoring occurrence of the maximum value.

Figure 4:
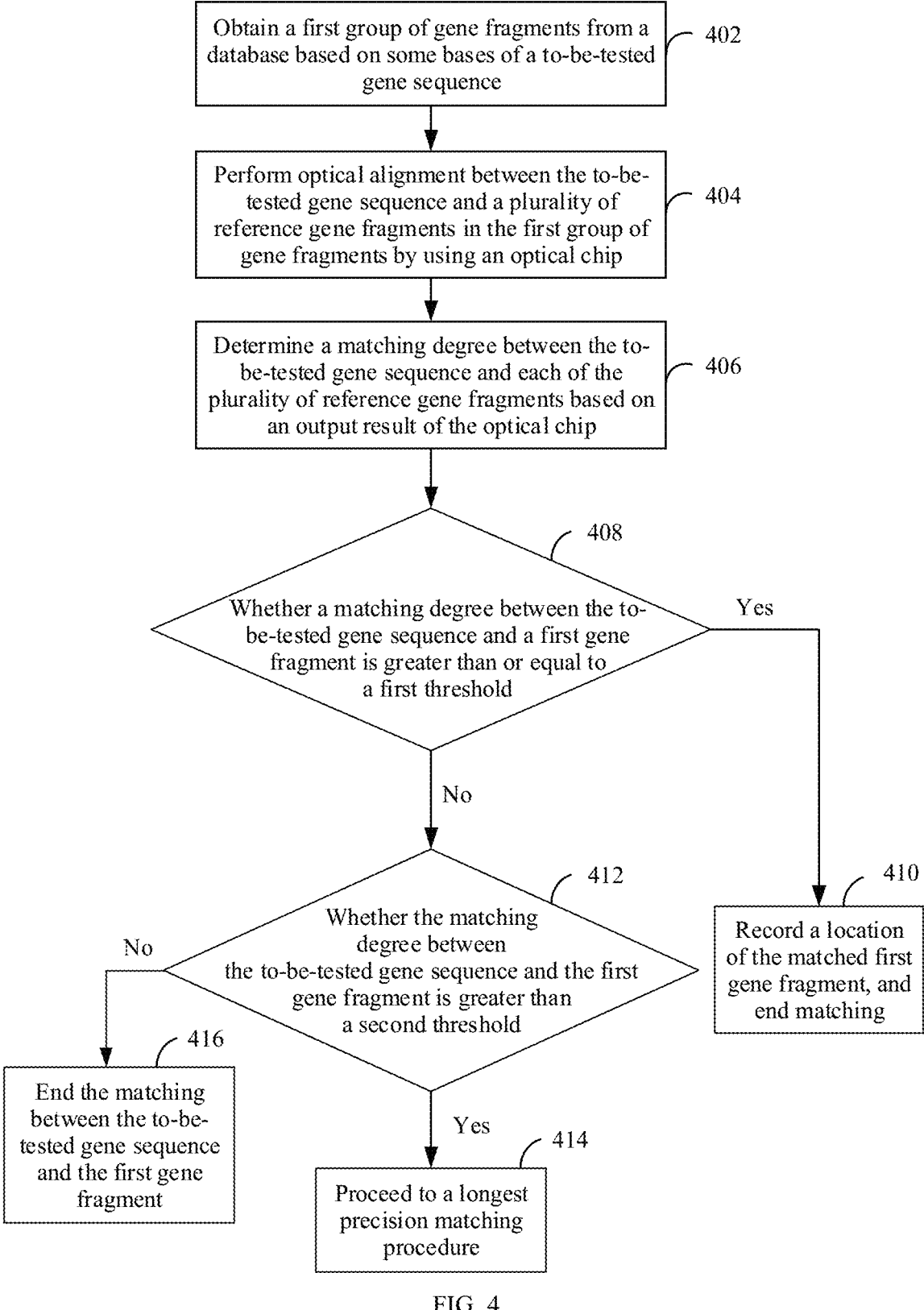
FIG. 4 is a flowchart of a gene alignment method according to an embodiment.

The following describes in detail how to implement gene alignment by using the gene alignment apparatus shown in FIG. 1, to increase a gene alignment speed. FIG. 4 is a flowchart of a gene alignment method according to an embodiment. The following specifically describes the method shown in FIG. 4 with reference to FIG. 1. For clear and simple description, in this embodiment, detecting one to-be-tested gene sequence is used as an example for description. It may be understood that, even if a plurality of to-be-tested gene sequences are tested at a time, alignment may be performed for each to-be-tested gene sequence with reference to the embodiments. As shown in FIG. 4, the method includes the following steps.

In step 402, the processor 102 obtains a first group of gene fragments from the database based on some bases of a to-be-tested gene sequence. Specifically, key of the to-be-tested gene sequence may be obtained in a manner of obtaining key 1044_1 of the gene database 1044. For example, five bases at the head of the to-be-tested gene sequence and five bases at the tail of the to-be-tested gene sequence may be used as key of the to-be-tested gene sequence. The gene database 1044 is searched based on key of the to-be-tested gene sequence, to obtain a plurality of values that match key, where the plurality of values are used to indicate possible locations of the to-be-tested gene sequence on a reference gene sequence. Because values corresponding to key in the gene database 1044 indicate location information of a corresponding reference gene fragment in the reference gene sequence, a plurality of reference gene fragments may be obtained based on a plurality of matched values. In this embodiment, a plurality of reference gene fragments that match key of the to-be-tested gene sequence are referred to as the first group of gene fragments.

Figure 5A:
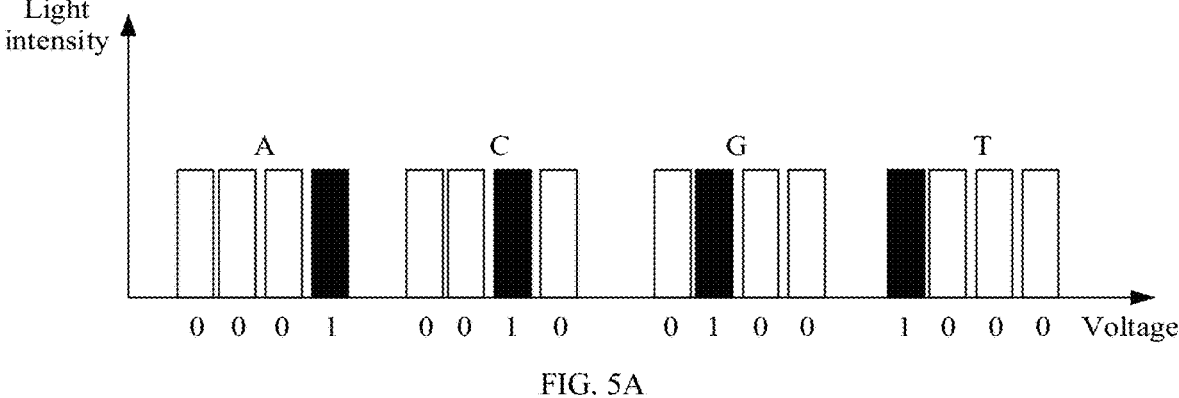
FIG. 5A, FIG. 5B, FIG. 5C, and FIG. 5D are examples of optical encoding according to an embodiment.

In step 404, optical alignment is performed between the to-be-tested gene sequence and the plurality of reference gene fragments in the first group of gene fragments by using the optical computing chip 106. Specifically, the processor 102 may separately perform optical encoding on the to-be-tested gene sequence and the plurality of reference gene segments, and load optical code of the to-be-tested gene sequence and optical code of the plurality of reference gene segments to the optical computing chip for alignment. In a process of performing optical encoding on the to-be-tested gene sequence and the reference gene fragments, base strings in the to-be-tested gene sequence and the reference gene fragments may be encoded respectively. For example, four point light sources are used as a unit cluster of single bases, and four different bases are represented by different degrees of brightness and darkness (0 indicates that the point light source is off, and 1 indicates that the point light source is bright). Coding schemes of A, C, G, and T are 0001, 0010, 0100, and 1000, as shown in FIG. 5A. According to encoding schemes of the single bases A, C, G, and T, the optical code of the to-be-tested gene sequence and the optical code of the plurality of reference gene fragments in the first group of gene fragments can be obtained. Therefore, the optical code of the to-be-tested gene sequence and the optical code of the plurality of reference gene fragments in the first group of gene fragments may be sent to the optical computing chip 106 to perform optical alignment.

Figure 5B:
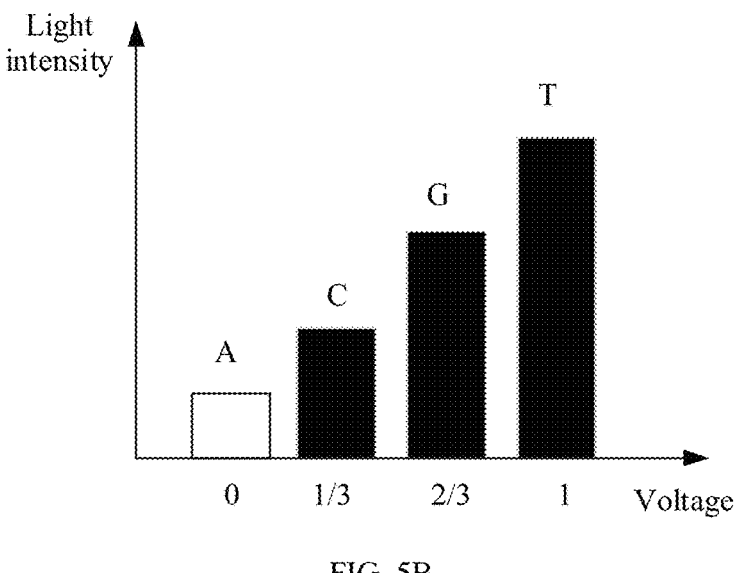
Figure 5C:
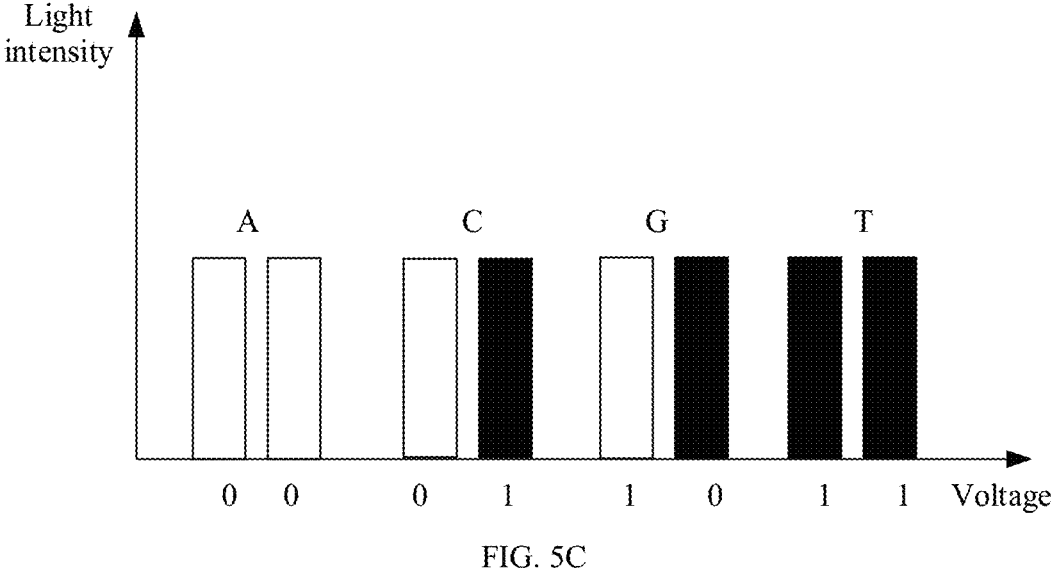
Figure 5D:
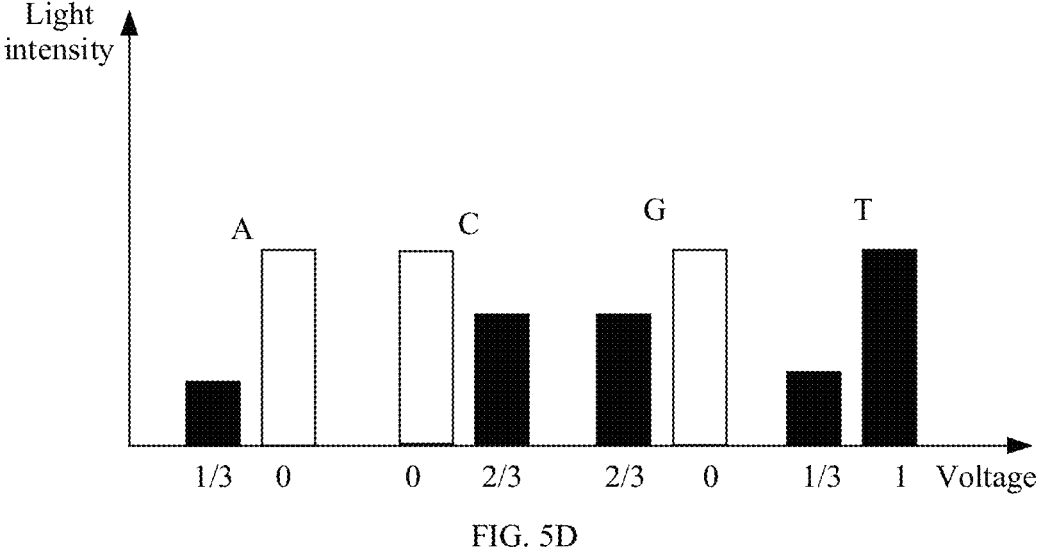

Different encoding schemes directly affect decoding difficulty and reliability of autocorrelation result output. In another case, light intensity information and/or light spatial information may be further included in an encoding process. In this embodiment, a manner of encoding by using the light intensity information may be referred to as an intensity encoding scheme, and a manner of encoding by using the light spatial information may be referred to as a spatial encoding scheme. The two encoding schemes may be further combined, and this combined manner may be referred to as a hybrid encoding scheme. In the intensity encoding scheme, a light intensity may be modulated by using different voltage amplitudes, and four different bases are represented by using light signals with different intensities. The intensity encoding scheme may be shown in FIG. 5B. In the spatial encoding scheme, a plurality of point light sources may be used as a unit cluster of single bases, and four different bases are represented by different degrees of brightness and darkness (0 indicates that the point light source is off, and 1 indicates that the point light source is bright). The spatial encoding scheme may be shown in FIG. 5C. A plurality of optical signals with a same voltage and different light intensities may be used to represent different bases. The hybrid encoding scheme may be a scheme of combining intensity encoding and spatial encoding. For example, the hybrid encoding scheme may be shown in FIG. 5D. A plurality of optical signals with specific different voltages and different light intensities may be combined to represent different bases. A specific encoding scheme is not limited in this embodiment.

In a process in which the optical computing chip 106 performs gene alignment, the light source array 202 may first send a first optical signal based on code of the reversed to-be-tested gene sequence, and Fourier transform is performed on the first optical signal after being reflected by the first concave mirror 208 to convert the first optical signal into a spectrum optical signal. The modulator array 204 receives the reflected spectrum optical signal of the first optical signal, and modulates the reflected spectrum optical signal of the first optical signal on the modulator array 204. Then, the light source array 202 separately sends a plurality of optical signals based on the optical code of the plurality of reference gene segments in the first group of reference gene segments, so that the optical signals sent based on the optical code of the reference gene segments pass through the first concave mirror 208 and are converted into spectrum optical signals at a location of the modulator array 204, and a multiplication operation is performed, in optical space, between the spectrum optical signals and the reflected signal of the first optical signal. The spectrum optical signals output by the modulator array 204 undergo inverse Fourier transform through the second concave mirror 210, and then are converted to time domain optical signals. Finally, the detector array 206 can separately obtain, by detecting light intensities of the time-domain optical signals output by the second concave mirror 210, matching results between the first optical signal and the optical signals of the plurality of reference gene fragments. A person skilled in the art may know that, an autocorrelation result of the two pieces of data is obtained by multiplying and performing inverse Fourier transform on spectrum data.

In step 406, the processor 102 determines a similarity degree between the to-be-tested gene sequence and each of the plurality of reference gene fragments based on an output result of the optical computing chip. After the detector array 206 obtains a matching result, the optical computing chip 106 may send the matching result to the processor 102. For example, a light intensity signal obtained through detection by the detector array 206 may be collected by using some peripheral circuits, the collected light intensity signal is converted into an electrical signal, the electrical signal is converted into a digital signal, and then the digital signal is sent to the processor 102. In this way, the processor 102 can obtain an alignment result between the to-be-tested gene sequence and the reference gene fragment from the optical computing chip 106. The detector array 206 may generate a feedback each time an alignment result is obtained, or may generate a feedback when the similarity degree reaches a preset threshold. It should be noted that, in this embodiment, the similarity degree is used to indicate a matching degree between the to-be-tested gene sequence and the reference gene fragment.

In step 408, the processor 102 determines whether a similarity degree between the to-be-tested gene segment and a first reference gene segment in the plurality of reference gene segments is greater than or equal to a first threshold, and if the similarity degree is greater than or equal to the first threshold, step 410 is proceeded. When it is determined that the similarity degree between the to-be-tested gene fragment and the first reference gene fragment is less than the first threshold, the method proceeds to step 412. In this step, after obtaining an alignment result, the processor 102 may compare the result with the set threshold. A matching result between the to-be-tested gene sequence and any reference gene segment may be aligned with the set threshold. In this embodiment, the to-be-tested gene sequence and the first reference gene fragment in the first group of reference gene fragments are used as an example for description, where the first reference gene fragment is any reference gene fragment in the first group of reference gene fragments. When the similarity degree between the to-be-tested gene fragment and the first reference gene fragment is greater than or equal to the first threshold, the method proceeds to step 410. Otherwise, the method proceeds to step 412.

In step 410, the processor 102 records a location of the first reference gene segment in the reference gene sequence, and ends matching on the to-be-tested gene sequence. In this embodiment, it may be considered that a matching result that the similarity degree is greater than or equal to the first threshold indicates that the matching is successful. When determining that the to-be-tested gene sequence successfully matches the first reference gene segment, the processor 102 may record the location of the first gene segment in the reference gene sequence, and end matching on the to-be-tested gene sequence. A matching process ends. It may be understood that, in this embodiment, the similarity degree is used to indicate the matching degree between the to-be-tested gene sequence and the reference gene fragment. The first threshold is used to indicate whether a matching criterion of a requirement is met. The first threshold may be used to indicate full matching, or may be used to indicate maximum similarity degree matching. If the similarity degree is greater than or equal to the set first threshold, it may be considered that the to-be-tested gene sequence matches the reference gene sequence or the to-be-tested gene sequence matches the reference gene sequence at a maximum similarity degree. For example, the first threshold may be 100%, or may be 95%. This is not limited herein.

If the processor determines that the similarity degree between the to-be-tested gene fragment and the first gene fragment is less than the first threshold in step 408, the processor 102 further determines whether the similarity degree between the to-be-tested gene fragment and the first gene fragment is greater than a second threshold in step 412. When the similarity degree between the to-be-tested gene fragment and the first gene fragment is greater than the second threshold, the method proceeds to step 414, namely, a maximum similarity degree matching procedure. Otherwise, the method proceeds to step 416. It is determined that the to-be-tested gene sequence does not match the first reference gene fragment, and the matching between the to-be-tested gene fragment and the first gene fragment ends. In this embodiment, the second threshold may be set to 50%. When the similarity degree between the to-be-tested gene fragment and the first reference gene fragment is less than the first threshold and greater than the second threshold, it indicates that there is a relatively high possibility that the to-be-tested gene sequence can match the reference gene sequence, in other words, some segments in the to-be-tested gene sequence may match the reference gene sequence. Therefore, the to-be-tested gene sequence needs to be further aligned with the reference gene sequence, and the method proceeds to the maximum similarity degree matching procedure.

It may be understood that step 408 to step 416 in FIG. 4 are described by using an example in which the to-be-tested gene sequence matches the first reference gene segment. After the similarity degree between the to-be-tested gene sequence and each of the plurality of reference gene fragments may be obtained by using step 404 and step 406, processing is performed according to step 408 and step 416 separately based on the similarity degree between the to-be-tested gene sequence and each reference gene fragment. After the first group of reference gene fragments is obtained, operations of step 404 to step 416 may also be sequentially performed on the to-be-tested gene sequence and each reference gene fragment in the first group of reference gene fragments. A specific implementation is not limited herein.

According to the gene alignment method provided in this embodiment, initial matching is performed on the to-be-tested gene sequence by using the constructed gene database, to screen out the first group of reference gene fragments that may match the to-be-tested gene sequence. A person skilled in the art knows that, a human reference gene segment is used as an example. The human reference gene segment has 3 billion bases, and it takes a lot of time to directly compare the to-be-tested gene segment with the reference gene segments one by one. However, after the to-be-aligned gene fragments are screened by using the gene database provided in this embodiment, reference gene fragments that need to be aligned may be reduced from 3 billion to several hundreds, thereby greatly reducing a quantity of reference gene fragments that need to be aligned. In addition, in this embodiment, after the first group of reference gene fragments is obtained, optical alignment is further performed between the to-be-tested gene sequence and the plurality of reference gene fragments in the first group of reference gene fragments by using the optical computing chip. An alignment speed of optical alignment performed by the optical computing chip is faster than an alignment speed of a method of electrical gene alignment. Therefore, the gene alignment method provided in this embodiment also greatly increases alignment efficiency.

Figure 6A:
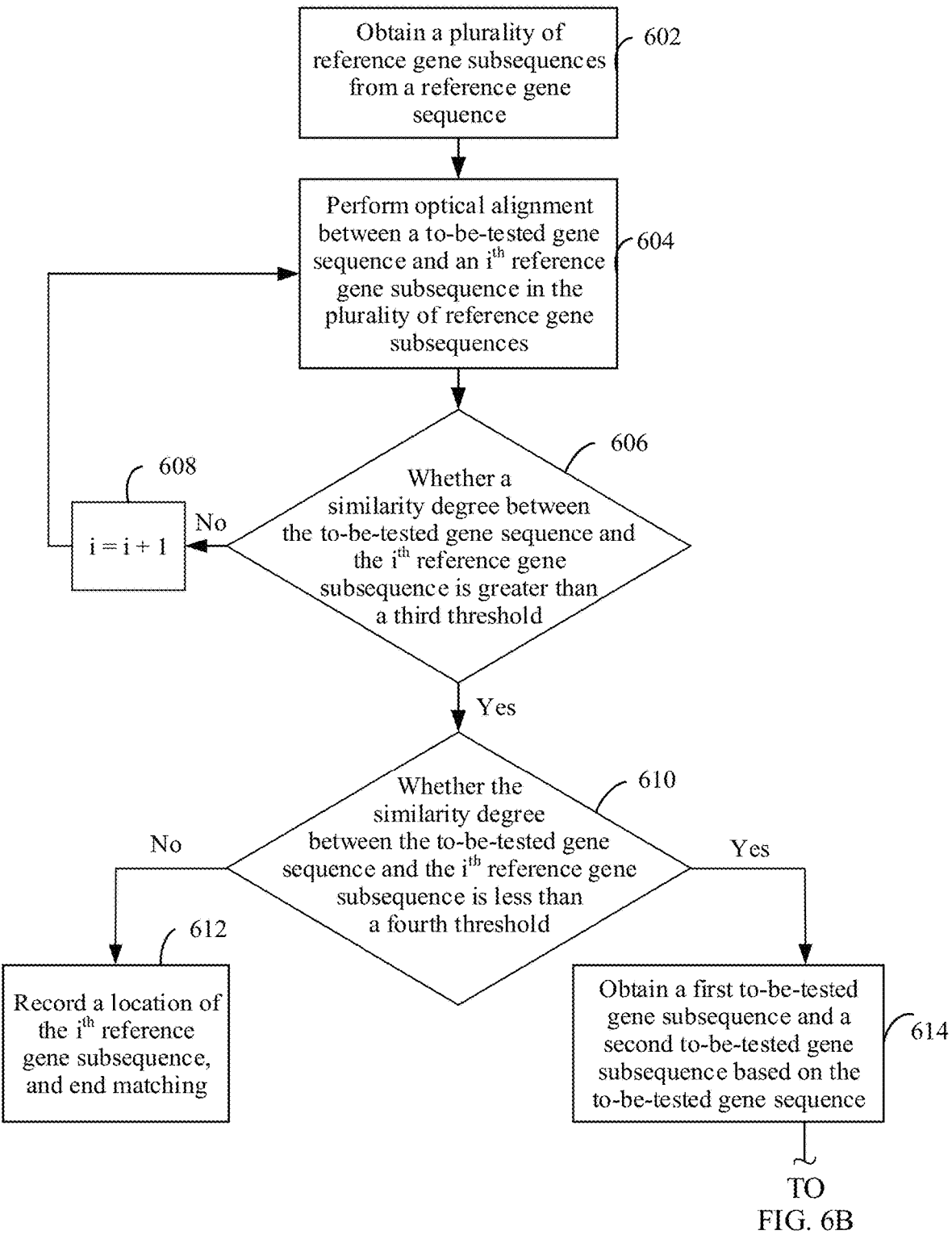
FIG. 6A to FIG. 6C are a flowchart of still another gene alignment method according to an embodiment.
Figure 6B:
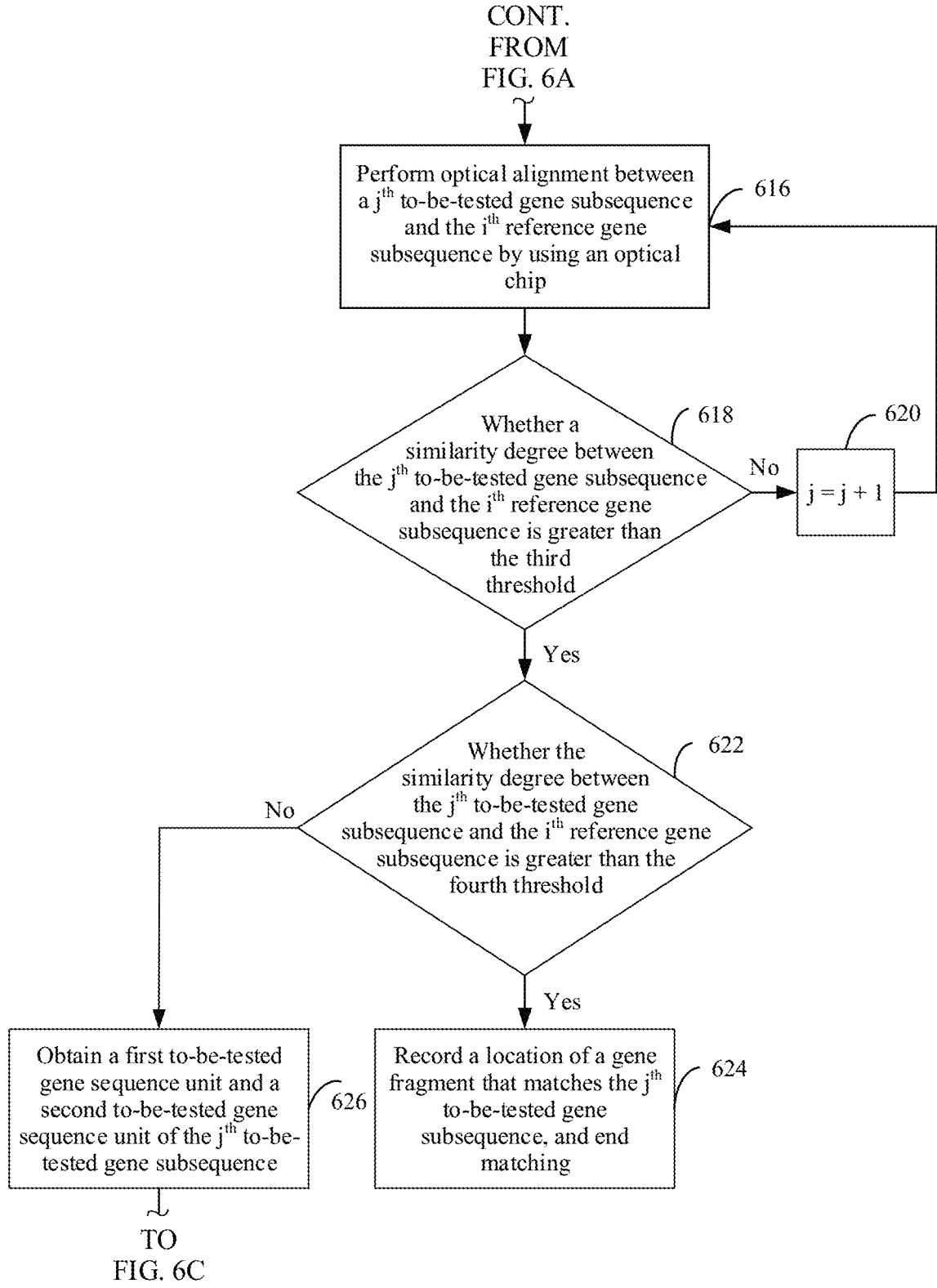
Figure 6C:
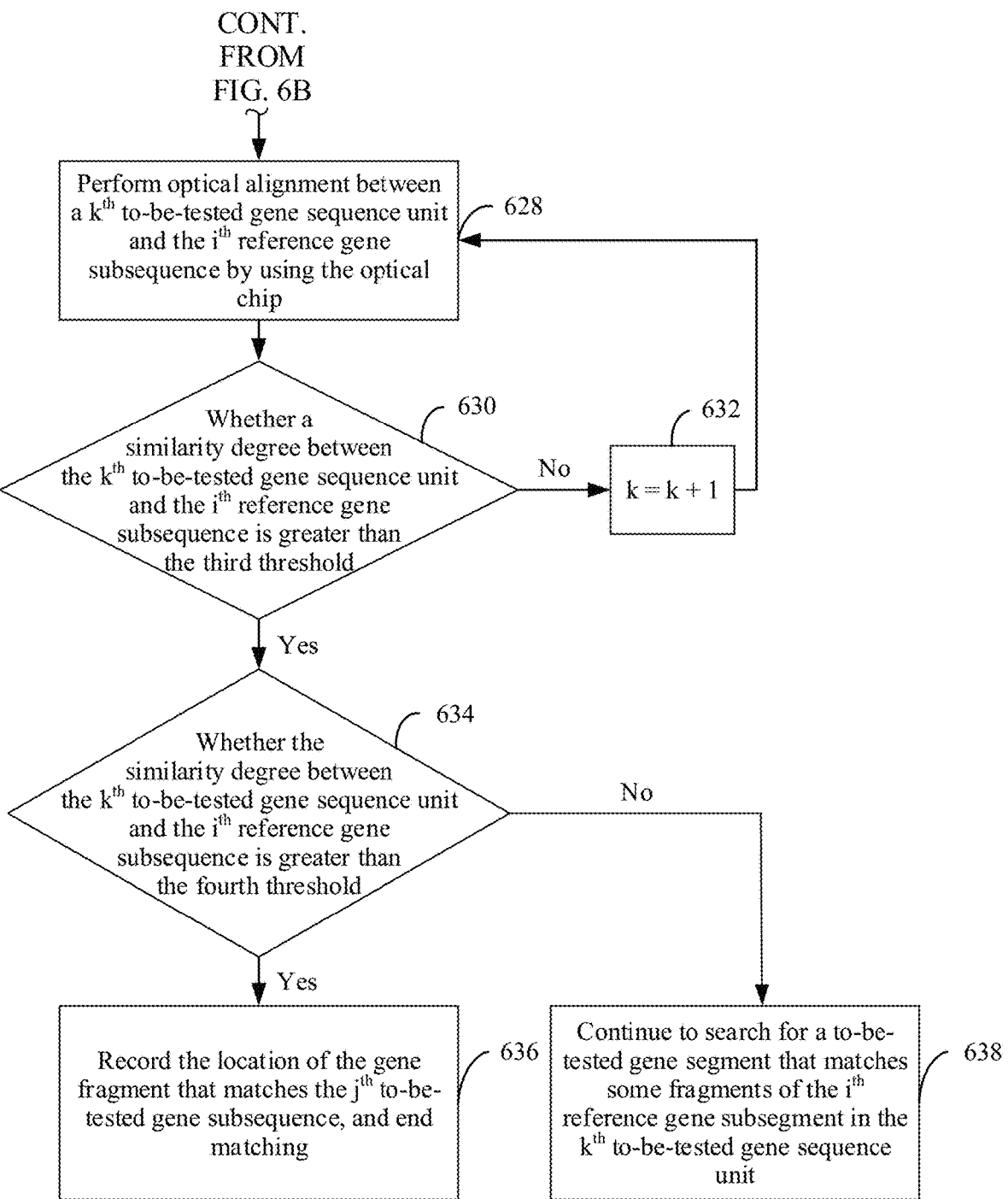

It should be noted that, in this embodiment, as long as a similarity degree between the to-be-tested gene sequence and any reference gene fragment in the first group of reference gene fragments is less than the first threshold and greater than the second threshold, the to-be-tested gene sequence may be further aligned according to a maximum similarity degree matching method shown in FIG. 6A to FIG. 6C. FIG. 6A to FIG. 6C are a flowchart of still another gene alignment method according to an embodiment. The method shown in FIG. 6A to FIG. 6C is still performed by the gene alignment apparatus 100. As shown in FIG. 6A to FIG. 6C, the method may include the following steps.

Figure 7:
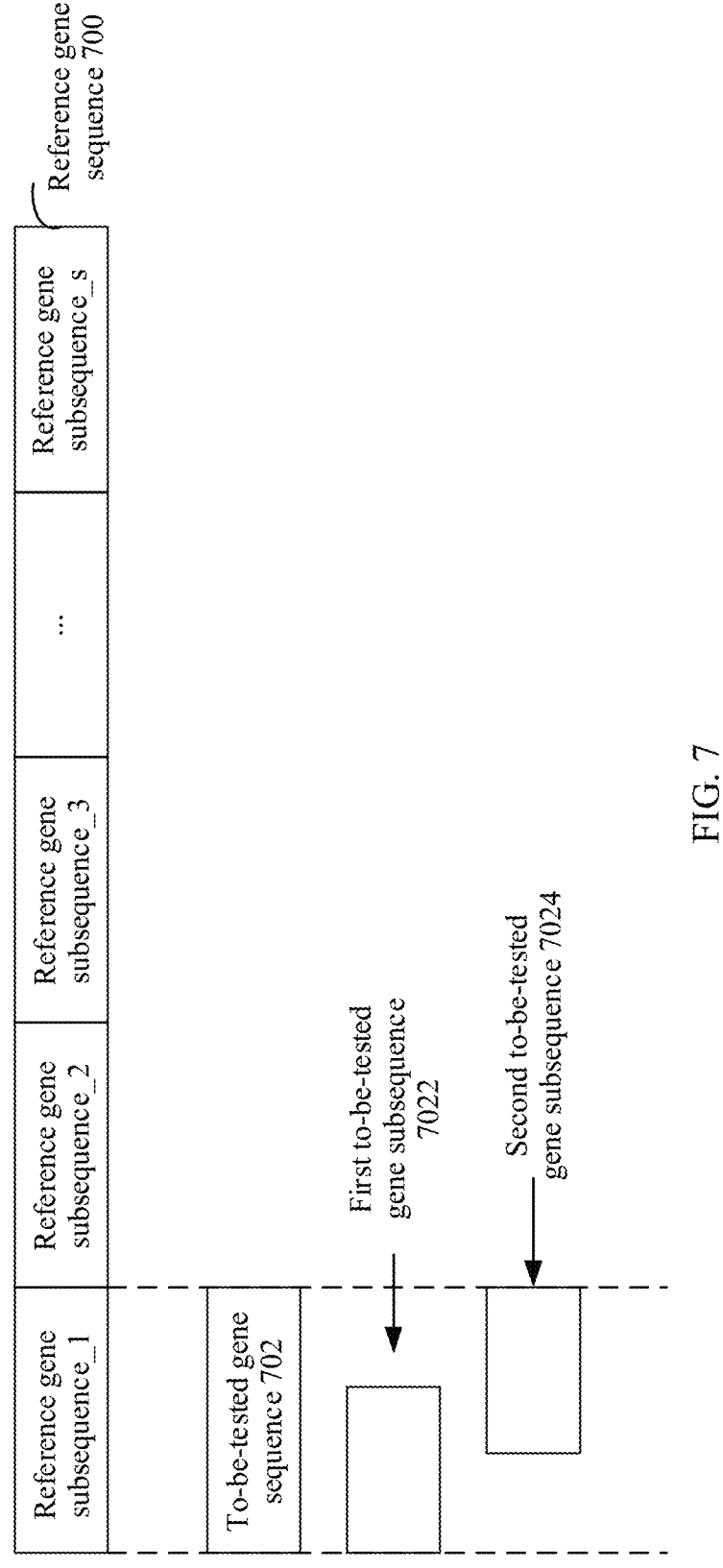
FIG. 7 is a schematic diagram of a reference gene subsequence and a to-be-tested gene subsequence according to an embodiment.

In step 602, the processor 102 obtains a plurality of reference gene subsequences from a reference gene sequence. Specifically, the processor 102 obtains the plurality of reference gene subsequences from the reference gene sequence based on a length of a to-be-tested gene sequence. For example, the plurality of reference gene subsequences may be obtained from the reference gene sequence by using the length of the to-be-tested gene sequence as a window and a sliding step. Alternatively, the reference gene sequence may be split into the plurality of reference gene subsequences based on a base length of the to-be-tested gene sequence. For example, as shown in FIG. 7, a plurality of reference gene subsequences may be obtained from the reference gene sequence 700 based on a length of the to-be-tested gene sequence 702. For example, the reference gene sequence has 3 billion bases. If the to-be-tested gene sequence has 150 bases, 0.2 million reference gene subsequences may be obtained.

In step 604, the to-be-tested gene sequence and an $i^{th}$ reference gene subsequence obtained in step 602 are input into the optical computing chip 106 to perform optical alignment. An initial value of i is 1, and a value of i is not greater than a quantity of reference gene subsequences obtained in step 602. Specifically, the processor 102 may separately perform optical encoding on the to-be-tested gene sequence and the $i^{th}$ reference gene subsequence; and load optical code of the to-be-tested gene sequence and optical code of the $i^{th}$ reference gene subsequence into the optical computing chip 106 to perform optical alignment, to obtain a similarity degree between the to-be-tested gene sequence and the $i^{th}$ reference gene subsequence. The optical computing chip 106 sends an alignment result to the processor 102. In this embodiment, a similarity degree between the to-be-tested gene sequence and a first reference gene subsequence in the plurality of reference gene subsequences may be referred to as a first similarity degree.

In step 606, the processor 102 determines whether the similarity degree between the to-be-tested gene sequence and the $i^{th}$ reference gene subsequence is greater than a set third threshold. If the similarity degree between the to-be-tested gene sequence and the $i^{th}$ reference gene subsequence is not greater than the third threshold, the to-be-tested gene sequence does not match the $i^{th}$ reference gene subsequence. The method proceeds to step 608, it is assumed that i=i+1, and the method returns to step 604. The to-be-tested gene sequence continues to be aligned with a next reference gene subsequence until optical alignment is completed between the to-be-tested gene sequence and all of the reference gene subsequences obtained in step 602 by using the optical computing chip 106. For example, if the processor 102 determines that the similarity degree between the to-be-tested gene sequence and the $i^{th}$ reference gene subsequence is greater than the third threshold in step 606, the method proceeds to step 610. In this embodiment, to find as much as possible a reference gene fragment that matches at least some fragments of the to-be-tested gene sequence, the third threshold may be set to a similarity degree less than 50%. For example, the third threshold may be set to 20%. The third threshold may alternatively be the same as the second threshold. This is not limited herein.

If the similarity degree between the to-be-tested gene sequence and the $i^{th}$ reference gene subsequence is greater than the third threshold, the processor 102 further determines whether the similarity degree between the to-be-tested gene sequence and the $i^{th}$ reference gene subsequence is greater than a fourth threshold in step 610. If the similarity degree between the to-be-tested gene sequence and the $i^{th}$ reference gene subsequence is greater than the fourth threshold, the method proceeds to step 612. In this embodiment, the fourth threshold is not greater than the first threshold, the first threshold may be a set threshold used to indicate full matching, and the fourth threshold is a threshold used to indicate maximum similarity degree matching. Generally, the first threshold may be set to 100%, and the fourth threshold may be set to 95%. The fourth threshold may alternatively be the same as the first threshold. For example, both the first threshold and the fourth threshold may be set to 95%, and are thresholds used to indicate maximum similarity degree matching. This is not limited herein. In step 612, the processor 102 determines that the $i^{th}$ reference gene subsequence is a gene fragment with a maximum similarity degree to the to-be-tested gene sequence, records a location of the $i^{th}$ reference gene subsequence in the reference gene sequence, and ends an alignment procedure of the to-be-tested gene sequence. If the similarity degree between the to-be-tested gene sequence and the $i^{th}$ reference gene subsequence is not greater than the fourth threshold, the method proceeds to step 614.

In step 614, the processor 102 obtains a first to-be-tested gene subsequence and a second to-be-tested gene subsequence based on the to-be-tested gene sequence. Continue to refer to FIG. 7. In this step, the processor 102 may obtain a first to-be-tested gene subsequence 7022 and a second to-be-tested gene subsequence 7024 based on the to-be-tested gene sequence 702. Some bases of the first to-be-tested gene subsequence 7022 are the same as some bases of the second to-be-tested gene subsequence 7024. For example, the first to-be-tested gene subsequence 7022 may include bases of a first preset length obtained from a head-to-tail direction of the to-be-tested gene sequence 702. The second to-be-tested gene subsequence 7024 may include bases of the first preset length obtained from a tail-to-head direction of the to-be-tested gene sequence 702. The some bases of the first to-be-tested gene subsequence 7022 are the same as the some bases of the second to-be-tested gene subsequence 7024. The method proceeds to step 616.

In step 616, optical alignment is performed between a $j^{th}$ to-be-tested gene subsequence and the $i^{th}$ reference gene subsequence by using the optical computing chip 106. An initial value of j is 1, and a value of j may not be greater than a quantity of to-be-tested gene subsequences. In this embodiment, two to-be-tested gene subsequences are obtained from the to-be-tested gene sequence. Therefore, in this embodiment, the value of j is not greater than 2. It may be understood that, if p (p is greater than 2) to-be-tested gene subsequences need to be obtained, the value of j may not be greater than p. In this step, the processor 102 also needs to first perform optical encoding on the $j^{th}$ to-be-tested gene subsequence and then load optical code of the $j^{th}$ to-be-tested gene subsequence and the optical code of the $i^{th}$ reference gene subsequence to the optical computing chip 106 to perform optical alignment, to obtain a similarity degree between the $j^{th}$ to-be-tested gene subsequence and the $i^{th}$ reference gene subsequence. The method proceeds to step 618. In step 618, the processor 102 determines whether the similarity degree between the $j^{th}$ to-be-tested gene subsequence and the $i^{th}$ reference gene subsequence is greater than the third threshold. If the similarity degree between the $j^{th}$ to-be-tested gene subsequence and the $i^{th}$ reference gene subsequence is not greater than the third threshold, the method proceeds to step 620, it is assumed that j=j+1, and then the method proceeds to step 616. Optical alignment is performed between the $(j+1)^{th}$ to-be-tested gene subsequence and the $i^{th}$ reference gene subsequence, to obtain a similarity degree between the $(j+1)^{th}$ to-be-tested gene subsequence and the $i^{th}$ reference gene subsequence. If the processor 102 determines that the similarity degree between the $j^{th}$ to-be-tested gene subsequence and the $i^{th}$ reference gene subsequence is greater than the third threshold in step 618, the method proceeds to step 622, to further determine whether the similarity degree between the $j^{th}$ to-be-tested gene subsequence and the $i^{th}$ reference gene subsequence is greater than the fourth threshold. In this embodiment, for clear and convenient description, a matching result the first to-be-tested gene subsequence and the first reference gene subsequence by the optical computing chip may be referred to as a second similarity degree. A matching result of the second to-be-tested gene subsequence and the first reference gene subsequence by the optical computing chip is referred to as a third similarity degree.

If the processor 102 determines that the similarity degree between the $j^{th}$ to-be-tested gene subsequence and the $i^{th}$ reference gene subsequence is greater than the fourth threshold in step 622, the method proceeds to step 624. A location of a reference gene segment that is in the $i^{th}$ reference gene subsequence and that matches the $j^{th}$ to-be-tested gene subsequence in the reference gene sequence is recorded, and matching on the to-be-tested gene sequence ends. If it is determined that similarity degrees between the $j^{th}$ to-be-tested gene subsequence and some segments of the $i^{th}$ reference gene subsequence are greater than the fourth threshold, to increase a matching speed, matching the $(j+1)^{th}$ to-be-tested gene subsequence with the $i^{th}$ reference gene subsequence may alternatively not continue, and an alignment procedure of the to-be-tested gene sequence is directly ended. Optical alignment may alternatively continue to be performed on the $(j+1)^{th}$ to-be-tested gene subsequence and the $i^{th}$ reference gene subsequence based on a requirement.

If the processor 102 determines that the similarity degree between the $j^{th}$ to-be-tested gene subsequence and the $i^{th}$ reference gene subsequence is not greater than the fourth threshold in step 622, the method proceeds to step 626. In step 626, the processor 102 obtains a first to-be-tested gene sequence unit and a second to-be-tested gene sequence unit of the $j^{th}$ to-be-tested gene subsequence, where some bases of the first to-be-tested gene sequence unit are the same as some bases of the second to-be-tested gene sequence unit. For details, refer to a method for obtaining the first to-be-tested gene subsequence and the second to-be-tested gene subsequence from the to-be-tested gene sequence in step 614. For example, the first to-be-tested gene sequence unit may include bases of a second preset length obtained from a head-to-tail direction of the $j^{th}$ to-be-tested gene subsequence. The second to-be-tested gene sequence unit may include bases of the second preset length obtained from a tail-to-head direction of the $j^{th}$ to-be-tested gene subsequence.

In step 628, optical alignment is performed between a $k^{th}$ to-be-tested gene sequence unit and the $i^{th}$ reference gene subsequence by using the optical computing chip 106. An initial value of k is 1, and a value of k is not greater than a quantity of to-be-tested gene sequence units. In this embodiment, because an example in which two to-be-tested gene sequence units are obtained based on the $j^{th}$ to-be-tested gene subsequence is used, the value of k is not greater than 2. Specifically, in step 628, the processor 102 may perform optical encoding on the $k^{th}$ to-be-tested gene sequence unit, and separately load optical code of the $k^{th}$ to-be-tested gene sequence unit and the optical code of the $i^{th}$ reference gene subsequence to the optical computing chip 106 to perform optical alignment. The method proceeds to step 630. In step 630, the processor 102 determines whether a similarity degree between the $k^{th}$ to-be-tested gene sequence unit and the $i^{th}$ reference gene subsequence is greater than the third threshold. If the similarity degree between the $k^{th}$ to-be-tested gene sequence unit and the $i^{th}$ reference gene subsequence is not greater than the third threshold, the method proceeds to step 632, it is assumed that k=k+1, and then the method proceeds to step 628. Optical alignment is performed between the second to-be-tested gene sequence unit and the $i^{th}$ reference gene subsequence by using the optical computing chip 106.

If the processor 102 determines that the similarity degree between the $k^{th}$ to-be-tested gene sequence unit and the $i^{th}$ reference gene subsequence is greater than the third threshold in step 630, the method proceeds to step 634. Whether the similarity degree between the $k^{th}$ to-be-tested gene sequence unit and the $i^{th}$ reference gene subsequence is greater than the fourth threshold is determined. If the similarity degree is greater than the fourth threshold, the method proceeds to step 636. A location of a gene fragment that is in the $i^{th}$ reference gene subsequence and that matches the $k^{th}$ to-be-tested gene sequence unit in the reference gene sequence is recorded, and matching is ended. Specifically, in one case, to increase a matching speed, after a gene fragment with a maximum similarity degree is obtained, matching on the to-be-tested gene sequence may be ended. In another case, matching on the $j^{th}$ to-be-tested gene subsequence may be ended, or matching on the $k^{th}$ to-be-tested gene sequence unit may be ended. Matching on the $(k+1)^{th}$ to-be-tested gene sequence unit or matching on the $(j+1)^{th}$ to-be-tested gene subsequence continues.

If the processor 102 determines that the similarity degree between the $k^{th}$ to-be-tested gene sequence unit and the $i^{th}$ reference gene subsequence is not greater than the fourth threshold in step 634, the method proceeds to step 638. The $k^{th}$ to-be-tested gene sequence unit continues to be split in a recursive manner, and optical alignment is performed between a subunit of the $k^{th}$ to-be-tested gene sequence unit and the $i^{th}$ reference gene subsequence, until a to-be-tested gene fragment whose similarity degree to the $i^{th}$ reference gene subsequence is greater than the fourth threshold is found. In this embodiment, a reference gene fragment whose similarity degree to some to-be-tested gene fragments in the to-be-tested gene sequence is greater than the fourth threshold may be referred to as a maximum similarity gene fragment.

According to the gene alignment method provided in this embodiment, for a to-be-tested gene segment that cannot be exactly matched by using FIG. 4, maximum similarity degree matching can be further performed on the to-betested gene segment by using the gene alignment method shown in FIG. 6A to FIG. 6C. The method shown in FIG. 6A to FIG. 6C can allow that the to-be-tested gene sequence is not consistent with the obtained maximum similarity gene fragment, and some bases in the to-be-tested gene sequence may be deleted or may be different from the reference gene fragment. Therefore, a deleted gene or a mutant gene in the to-be-tested gene sequence can be exactly located.

Figure 8:
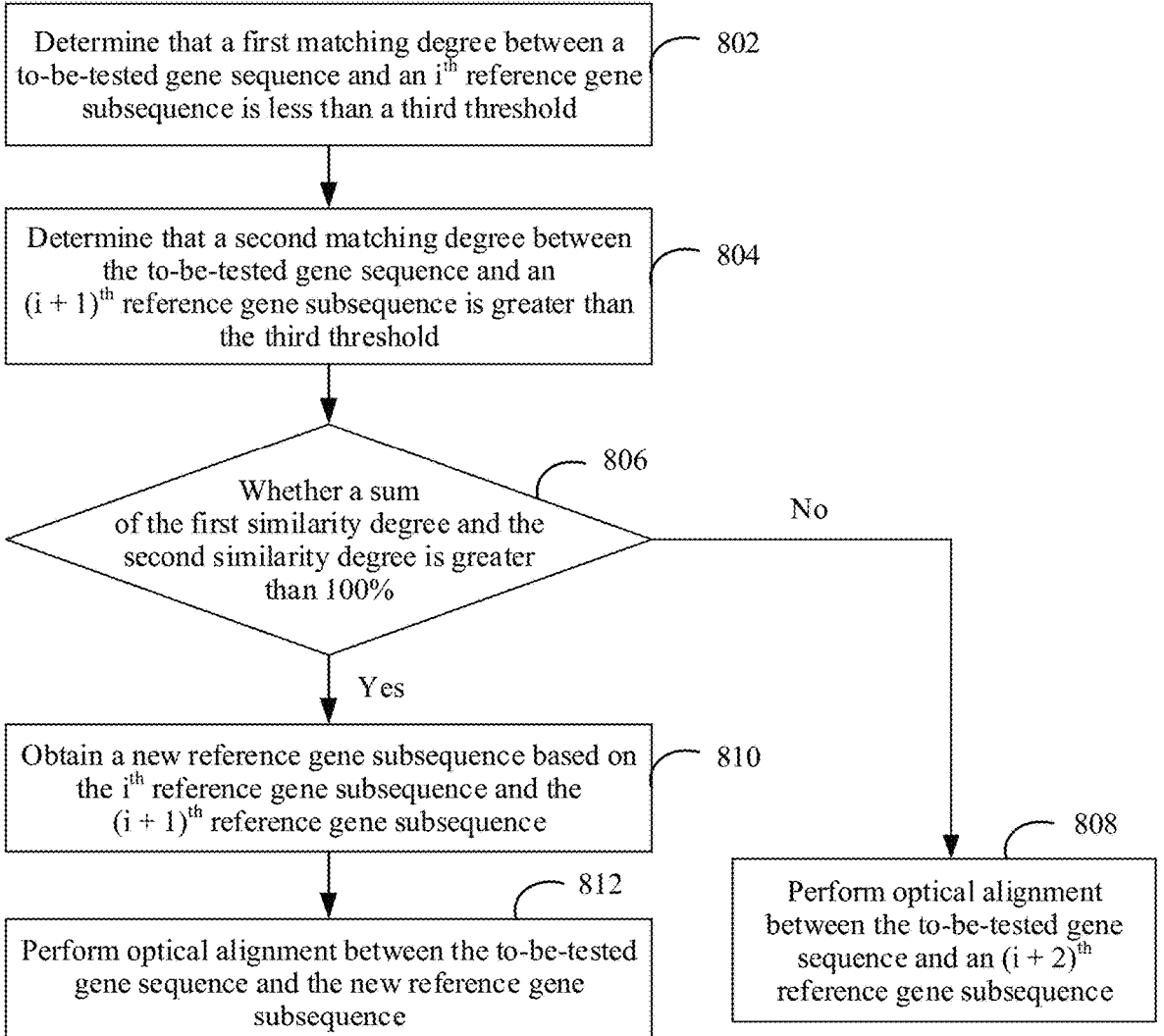
FIG. 8 is a flowchart of still another gene alignment method according to an embodiment.

In still another case, the gene alignment method provided in this embodiment may further include a method procedure shown in FIG. 8. The method shown in FIG. 8 may be after step 604 shown in FIG. 6A to FIG. 6C. As shown in FIG. 8, the method may include the following steps. In step 802, the processor 102 determines that a first similarity degree between the to-be-tested gene sequence and the $i^{th}$ reference gene subsequence is less than a third threshold. In addition, in step 804, when the processor 102 further determines that a second similarity degree between the to-be-tested gene sequence and the $(i+1)^{th}$ reference gene subsequence is greater than the third threshold, the method proceeds to step 806. It should be noted that, for descriptions of step 802 and step 804, refer to descriptions of step 606 in FIG. 6A to FIG. 6C. The third threshold may be the same as the third threshold set in step 606, for example, may be 50%.

In step 806, the processor further determines whether a sum of the first similarity degree and the second similarity degree is greater than 100%. If the sum of the first similarity degree and the second similarity degree is not greater than 100%, the method proceeds to step 808. Optical alignment is performed between the to-be-tested gene sequence and the $(i+2)^{th}$ reference gene subsequence by using the optical computing chip 106. If the sum of the first similarity degree and the second similarity degree is greater than 100%, the method proceeds to step 810. In step 810, the processor 102 obtains a new reference gene subsequence based on the $i^{th}$ reference gene subsequence and the $(i+1)^{th}$ reference gene subsequence. In step 810, some reference gene fragments may be obtained from the $i^{th}$ reference gene subsequence and some reference gene fragments may be obtained from the $(i+1)^{th}$ reference gene subsequence based on a ratio of the first similarity degree to the second similarity degree to constitute the new reference gene subsequence. For example, if the first similarity degree is 40% and the second similarity degree is 80%, and a length of a reference gene sequence is 150 base pairs, 50 base pairs at the tail of the $i^{th}$ reference gene subsequence and 100 base pairs at the head of the $(i+1)^{th}$ reference gene subsequence may constitute a new continuous reference subsequence with a length of 150 base pairs. After the new reference subsequence is obtained, the method proceeds to step 812. Optical alignment is performed between the to-be-tested gene sequence and the obtained new reference subsequence by using the optical computing chip 106. For a specific optical alignment method, refer to the descriptions of step 604 in FIG. 6A to FIG. 6C. In addition, in a process of aligning on the to-be-tested gene sequence with the obtained new reference subsequence, refer to a process of aligning the to-be-tested gene sequence with the $i^{th}$ reference subsequence in FIG. 6A to FIG. 6C. In this manner, if a similarity degree between the to-be-tested gene sequence and the new reference gene subsequence is greater than the third threshold, reference may continue to be made to the method in step 610 to step 638 in FIG. 6A to FIG. 6C. The new reference subsequence is searched for a reference gene fragment whose similarity degree to the to-be-tested gene sequence is greater than the fourth threshold. In this embodiment, a reference gene fragment found in the reference gene sequence according to the alignment method shown in FIG. 6A to FIG. 6C and FIG. 8 and whose similarity degree to the to-be-tested gene sequence is greater than the fourth threshold may be referred to as a maximum similarity gene fragment.

The method shown in FIG. 8 may be used in combination with the method shown in FIG. 6A to FIG. 6C. For example, when it is determined that the similarity degree between the to-be-tested gene sequence and the $i^{th}$ reference gene subsequence is relatively low, and the similarity degree between the to-be-tested gene sequence and the $(i+1)^{th}$ reference gene subsequence is relatively high, the method shown in FIG. 8 may be performed instead. Therefore, the new reference gene sequence obtained from the $i^{th}$ reference gene subsequence and the $(i+1)^{th}$ reference gene subsequence can be aligned with the to-be-tested gene sequence. In this manner of adjusting the reference gene subsequence in time based on a partial alignment result, a probability and a speed of obtaining the maximum similarity gene segment can be increased, and a quantity of alignment times can be reduced. After the to-be-tested gene sequence is first aligned with the plurality of reference gene subsequences obtained in step 602 according to the method shown in FIG. 6A to FIG. 6C, the method shown in FIG. 8 is performed to adjust the reference gene subsequence and perform alignment. A specific execution mode is not limited in this embodiment.

It should be noted that FIG. 8 is described by using the to-be-tested gene sequence and the $i^{th}$ reference gene subsequence as an example. The $i^{th}$ reference gene subsequence may be any one of the plurality of reference gene subsequences. For example, in step 802, the processor may perform alignment between the to-be-tested gene sequence and a second reference gene subsequence in the plurality of reference gene subsequences. A similarity degree between the to-be-tested gene sequence and the second reference gene subsequence is a fourth similarity degree, and the fourth similarity degree is less than the third threshold. In step 804, the processor 102 determines that a similarity degree between the to-be-tested gene sequence and a third reference gene subsequence in the plurality of reference gene subsequences is a fifth similarity degree, and the fifth similarity degree is greater than the third threshold. If the processor further determines that a sum of the fourth similarity degree and the fifth similarity degree is greater than 100% in step 806, the processor 102 may obtain a new reference gene subsequence based on the second reference gene subsequence and the third reference gene subsequence by using the method shown in FIG. 8.

In this embodiment, after the maximum similarity gene segment of the to-be-tested gene sequence is found by using the methods in FIG. 6A to FIG. 6C and FIG. 8, the maximum similarity gene segment may be further extended on the to-be-tested gene sequence and the reference sequence by using a Smith-Waterman local alignment algorithm, to obtain a longer maximum similarity gene fragment, so as to facilitate further gene analysis of the to-be-tested gene fragment.

It may be understood that, the method shown in the foregoing embodiment is described by using an example in which the to-be-tested gene sequence is aligned with one of the plurality of reference gene subsequences. Alignment may be performed separately between the to-be-tested gene sequence and the plurality of reference gene subsequences. This is not limited herein. Ordinal numerals such as "first" and "second" in the embodiments are used to distinguish between a plurality of objects, and are not intended to limit a sequence, a time sequence, priorities, or importance degrees of the plurality of objects.

Figure 9:
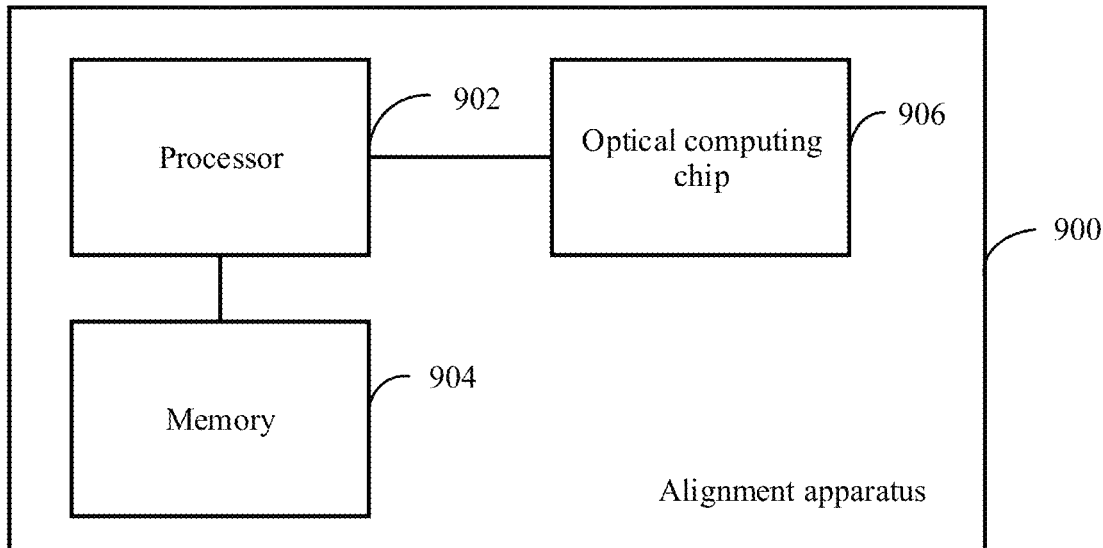
FIG. 9 is a schematic structural diagram of an alignment apparatus according to an embodiment.

It may be understood that the alignment method in the embodiments merely uses gene alignment as an example. An alignment method that is provided in the embodiments and that combines an electrical alignment method implemented based on a database and optical alignment method performed based on the optical computing chip may be further applied to various other scenarios. FIG. 9 is a schematic diagram of an alignment apparatus according to an embodiment. The alignment apparatus may be configured to implement various data alignment scenarios including gene alignment.

As shown in FIG. 9, the alignment apparatus 900 may include a processor 902, a memory 904, and an optical computing chip 906. The processor 902 is configured to obtain, based on a to-be-matched first object, a first group of reference objects from a database stored in the memory 904, where the first group of reference objects includes a plurality of reference objects whose some features are the same as some features of the first object. The optical computing chip 906 is configured to connect to the processor and perform optical alignment between the first object and the plurality of reference objects. The processor 902 may be further configured to determine a similarity degree between the first object and each of the plurality of reference objects based on an output result of the optical computing chip.

In another case, the processor 902 may be further configured to: determine, based on the output result of the optical computing chip, that a similarity degree between the first object and a first reference object in the first group of reference objects is less than a first threshold and greater than a second threshold; and obtain a plurality of reference sub-objects based on a standard object, where each reference sub-object is a part of the reference object. The optical computing chip 906 may be further configured to perform optical alignment between the first object and a first reference sub-object in the plurality of reference sub-objects, to obtain a first similarity degree between the first object and the first reference sub-object.

In still another case, the processor 902 may be further configured to: determine that the first similarity degree is greater than a third threshold and less than a fourth threshold; and in response to the determining, obtain a first sub-object and a second sub-object based on the first object, where the fourth threshold is not greater than the first threshold, and some data of the first sub-object is the same as some data of the second sub-object. The optical computing chip 906 may be further configured to: perform optical alignment between the first sub-object and the first reference sub-object to obtain a second similarity degree; and perform optical alignment between the second sub-object and the first reference sub-object to obtain a third similarity degree. The processor 902 may be further configured to: when the second similarity degree is greater than the fourth threshold, record a location of the first reference sub-object in the standard object.

It may be understood that the alignment apparatus shown in FIG. 9 may be configured to implement functions of the alignment apparatus shown in FIG. 1, and descriptions of the alignment apparatus in FIG. 9 may refer to the descriptions in FIG. 1 to FIG. 8 in the embodiments. The alignment apparatus shown in FIG. 9 may be applied to various scenarios in which data alignment or feature alignment needs to be performed, including gene alignment. It may be said that the gene alignment apparatus shown in FIG. 1 is a specific application of the alignment apparatus shown in FIG. 9. It should be noted that the alignment apparatus shown in FIG. 9 and the alignment method provided in the embodiments may be further applied to scenarios such as picture alignment, reverse image search, sequence alignment, and fuzzy matching. This is not limited herein.

Figure 10:
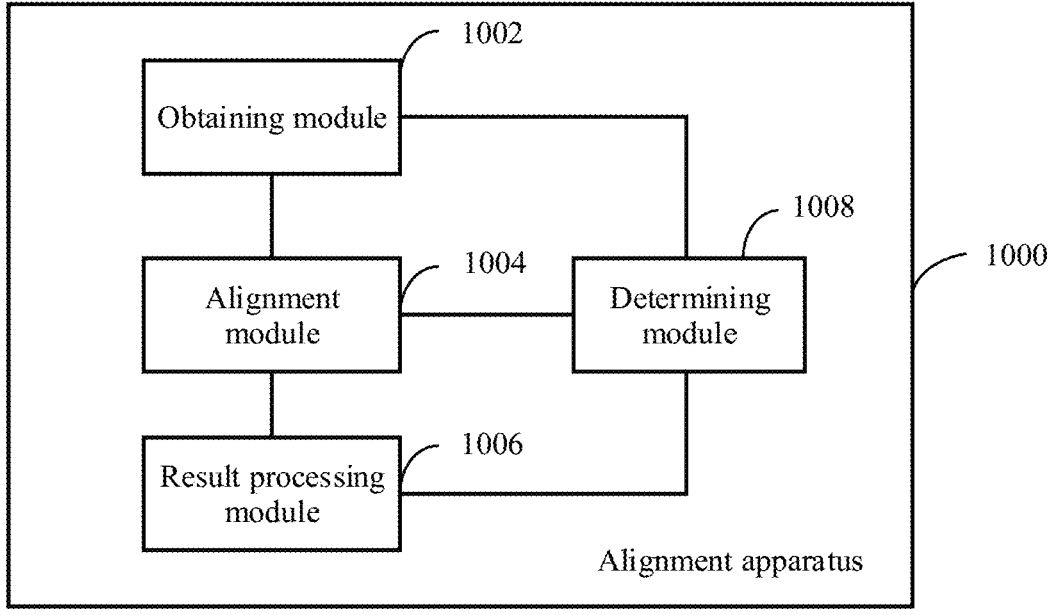
FIG. 10 is a schematic structural diagram of still another alignment apparatus according to an embodiment.

FIG. 10 is a schematic diagram of another alignment apparatus according to an embodiment. As shown in FIG. 10, the alignment apparatus 1000 may include an obtaining module 1002, an alignment module 1004, and a result processing module 1006. The obtaining module 1002 is configured to obtain a first group of gene fragments from a database based on a to-be-tested gene sequence, where the database system includes a plurality of reference gene fragments of a reference gene sequence, and the first group of gene fragments includes a plurality of reference gene fragments that match some bases of the to-be-tested gene sequence. The alignment module 1004 is configured to perform optical alignment between the to-be-tested gene sequence and the plurality of reference gene fragments in the first group of gene fragments. The result processing module 1006 is configured to determine a similarity degree between the to-be-tested gene sequence and each of the plurality of reference gene fragments in the first group of gene fragments based on an output result of the alignment module 1004.

In another case, the alignment apparatus 1000 may further include a determining module 1008. The determining module 1008 is configured to determine, based on an output result of the alignment module 1004, that a similarity degree between the to-be-tested gene sequence and a first gene fragment in the first group of gene fragments is less than a first threshold and greater than a second threshold. The obtaining module 1002 is further configured to: when the determining module 1008 determines that the similarity degree between the to-be-tested gene sequence and the first gene fragment in the first group of gene fragments is less than the first threshold and greater than the second threshold, obtain a plurality of reference gene subsequences from the reference gene sequence, where each reference gene subsequence is a part of the reference gene sequence. The alignment module 1004 is further configured to perform optical alignment between the to-be-tested gene sequence and a first reference gene subsequence in the plurality of reference gene subsequences. The result processing module 1006 is further configured to obtain a first similarity degree between the to-be-tested gene sequence and the first reference gene subsequence based on an output result of the optical computing chip.

In still another case, the determining module 1008 is further configured to determine that the first similarity degree is greater than a third threshold and less than a fourth threshold, where the fourth threshold is not greater than the first threshold. The obtaining module 1002 is further configured to: in response to the determining of the determining module 1008, obtain a first to-be-tested gene subsequence and a second to-be-tested gene subsequence based on the to-be-tested gene sequence, where some bases of the first to-be-tested gene subsequence are the same as some bases of the second to-be-tested gene subsequence. The alignment module 1004 is further configured to: perform optical alignment between the first to-be-tested gene subsequence and the first reference gene subsequence to obtain a second similarity degree; and perform optical alignment between the second to-be-tested gene subsequence and the first reference gene subsequence to obtain a third similarity degree.

In still another case, the result processing module 1006 is further configured to: when the second similarity degree is greater than the fourth threshold, record a location of the first reference gene subsequence in the reference gene sequence.

In still another case, the obtaining module 1002 is further configured to: when the determining module 1008 determines that the third similarity degree is greater than the third threshold and less than the fourth threshold, obtain a first to-be-tested gene subsequence unit and a second to-be-tested gene subsequence unit based on the second to-be-tested gene subsequence. Some bases of the first to-be-tested gene subsequence unit are the same as some bases of the second to-be-tested gene subsequence unit. The alignment module 1004 is further configured to perform optical alignment between the first to-be-tested gene subsequence unit and the first reference gene subsequence, and perform optical alignment between the second to-be-tested gene subsequence unit and the first reference gene subsequence.

In still another case, the alignment module 1004 is further configured to: perform optical alignment between the to-be-tested gene sequence and a second reference gene subsequence in the plurality of reference gene subsequences, to obtain a fourth similarity degree between the to-be-tested gene sequence and the second reference gene subsequence; and perform optical alignment between the to-be-tested gene sequence and a third reference gene subsequence in the plurality of reference gene subsequences, to obtain a fifth similarity degree between the to-be-tested gene sequence and the third reference gene subsequence, where the third reference gene subsequence is a reference gene subsequence immediately adjacent to the second reference gene subsequence. When the determining module 1008 determines that a sum of the fourth similarity degree and the fifth similarity degree is greater than the first threshold, the obtaining module 1002 is further configured to obtain a fourth reference gene subsequence based on the second reference gene subsequence and the third reference gene subsequence, where the fourth reference gene subsequence includes some bases of the second reference gene subsequence and some bases of the third reference gene subsequence. The alignment module 1004 is further configured to input the to-be-tested gene sequence and the fourth reference gene subsequence into the optical computing chip to perform optical alignment.

In still another case, the result processing module 1006 is further configured to: determine, based on an output result of the optical computing chip, that a second gene fragment in the first group of gene fragments matches the to-be-tested gene sequence; and record a location of the second gene fragment in the reference gene sequence.

It may be understood that the alignment apparatus shown in FIG. 10 may be configured to implement functions of the gene alignment apparatus shown in FIG. 1. For details, refer to the foregoing descriptions of the functions of related modules in FIG. 1. Details are not described herein again. It may be understood that the described apparatus embodiments are merely examples. For example, division into the modules is merely logical function division and may be other division in an actual implementation. For example, a plurality of modules or components may be combined or integrated into another system, or some features may be ignored or not performed. In addition, connections between the modules discussed in the foregoing embodiments may be implemented in electrical, mechanical, or other forms. The modules described as separate components may or may not be physically separate. A component displayed as a module may or may not be a physical module. In addition, functional modules in the embodiments may exist independently, or may be integrated into one processing module.

An embodiment further provides a computer program product for implementing gene alignment, including a computer-readable storage medium that stores program code. Instructions included in the program code are used to perform the method procedure described in any one of the foregoing method embodiments. An ordinary person skilled in the art may understand that the foregoing storage medium includes any non-transitory machine-readable medium capable of storing program code, for example, a USB flash drive, a removable hard disk, a magnetic disk, an optical disc, a random access memory RAM), a solid-state drive (SSD), or a non-volatile memory.

It should be noted that the embodiments provided in this disclosure are merely examples. A person skilled in the art may clearly know that, for convenience and conciseness of description, in the foregoing embodiments, the embodiments emphasize different aspects, and for a part not described in detail in an embodiment, refer to related description of another embodiment. The features disclosed in the embodiments, claims, and the accompanying drawings may exist independently or exist in a combination. Features described in a hardware form in the embodiments be executed by software, and vice versa. This is not limited herein.

---

What is claimed is:

1. A gene alignment method implemented by a computer system comprising an optical computing chip, the gene alignment method comprising:

obtaining reference gene fragments from a gene database based on a to-be-tested gene sequence, wherein the gene database comprises a reference gene sequence, wherein the reference gene sequence comprises the reference gene fragments, and wherein the reference gene fragments match some bases of the to-be-tested gene sequence;

inputting the to-be-tested gene sequence and the reference gene fragments into the optical computing chip;

performing a first optical alignment of the to-be-tested gene sequence and the reference gene fragments using the optical computing chip;

determining, based on an output result of the first optical alignment, that a similarity degree between the to-be-tested gene sequence and a first gene fragment in the reference gene fragments is less than a first threshold and greater than a second threshold;

obtaining a plurality of reference gene subsequences from the reference gene sequence, wherein the reference gene subsequences comprise a first reference gene subsequence;

inputting the to-be-tested gene sequence and the first reference gene subsequence into the optical computing chip;

performing a second optical alignment of the to-be-tested gene sequence and the first reference gene subsequence to obtain a first similarity degree between the to-be-tested gene sequence and the first reference gene subsequence;

making a determination that the first similarity degree is greater than a third threshold and less than a fourth threshold, wherein the fourth threshold is not greater than the first threshold;

obtaining, in response to the determination, a first to-be-tested gene subsequence and a second to-be-tested gene subsequence based on the to-be-tested gene sequence, wherein some bases of the first to-be-tested gene subsequence are the same as some bases of the second to-be-tested gene subsequence;

inputting the first to-be-tested gene subsequence and the first reference gene subsequence into the optical computing chip;

performing a third optical alignment of the first to-be-tested gene subsequence and the first reference gene subsequence to obtain a second similarity degree;

inputting the second to-be-tested gene subsequence and the first reference gene subsequence into the optical computing chip; and performing a fourth optical alignment of the second to-be-tested gene subsequence and the first reference gene subsequence to obtain a third similarity degree.

2. The gene alignment method of claim 1, further comprising recording, when the second similarity degree is greater than the fourth threshold, a location of the first reference gene subsequence in the reference gene sequence.

3. The gene alignment method of claim 1, further comprising:

obtaining, when the third similarity degree is greater than the third threshold and less than the fourth threshold, a first to-be-tested gene subsequence unit and a second to-be-tested gene subsequence unit based on the second to-be-tested gene subsequence, wherein some bases of the first to-be-tested gene subsequence unit are the same as some bases of the second to-be-tested gene subsequence unit;

inputting the first to-be-tested gene subsequence unit and the first reference gene subsequence into the optical computing chip;

performing a fifth optical alignment of the first to-be-tested gene subsequence unit and the first reference gene subsequence;

inputting the second to-be-tested gene subsequence unit and the first reference gene subsequence into the optical computing chip; and performing a sixth optical alignment of the second to-be-tested gene subsequence unit and the first reference gene subsequence.

4. The gene alignment method of claim 1, further comprising:

determining, based on the output result, that a first reference gene fragment of the reference gene fragments matches the to-be-tested gene sequence; and recording a location of the first reference gene fragment in the reference gene sequence.

5. The gene alignment method of claim 1, wherein inputting the to-be-tested gene sequence and the reference gene fragments comprises:

separately performing optical encoding on the to-be-tested gene sequence and the reference gene fragments; and separately inputting optical code of the to-be-tested gene sequence and optical code of the reference gene fragments into the optical computing chip.

6. The gene alignment method of claim 1, further comprising further obtaining the reference gene fragments from the gene database based on first m bases and last n bases of the to-be-tested gene sequence, wherein m and n are greater than 0, and wherein a sum of m and n is less than a quantity of bases in the to-be-tested gene sequence.

7. A gene alignment apparatus comprising:

a processor configured to:

obtain reference gene fragments from a gene database based on a to-be-tested gene sequence, wherein the gene database comprises a reference gene sequence, wherein the reference gene sequence comprises the reference gene fragments, and wherein the reference gene fragments match some bases of the to-be-tested gene sequence;

determine, based on an output result of a first optical alignment, that a similarity degree between the to-be-tested gene sequence and a first gene fragment in the reference gene fragments is less than a first threshold and greater than a second threshold;

obtain a plurality of reference gene subsequences from the reference gene sequence, wherein the reference gene subsequences comprise a first reference gene subsequence;

make a determination that a first similarity degree is greater than a third threshold and less than a fourth threshold, wherein the fourth threshold is not greater than the first threshold; and obtain, in response to the determination, a first to-be-tested gene subsequence and a second to-be-tested gene subsequence based on the to-be-tested gene sequence, wherein some bases of the first to-be-tested gene subsequence are the same as some bases of the second to-be-tested gene subsequence, and an optical computing chip coupled to the processor and configured to:

input the to-be-tested gene sequence and the reference gene fragments;

perform the first optical alignment of the to-be-tested gene sequence and the reference gene fragments;

input the to-be-tested gene sequence and the first reference gene subsequence;

perform a second optical alignment of the to-be-tested gene sequence and the first reference gene subsequence to obtain the first similarity degree between the to-be-tested gene sequence and the first reference gene subsequence;

input the first to-be-tested gene subsequence and the first reference gene subsequence;

perform a third optical alignment of the first to-be-tested gene subsequence and the first reference gene subsequence to obtain a second similarity degree;

input the second to-be-tested gene subsequence and the first reference gene subsequence; and perform a fourth optical alignment between the second to-be-tested gene subsequence and the first reference gene subsequence to obtain a third similarity degree.

8. The gene alignment apparatus of claim 7, wherein the processor is further configured to record, when the second similarity degree is greater than the fourth threshold, a location of the first reference gene subsequence in the reference gene sequence.

9. The gene alignment apparatus of claim 7, wherein the processor is further configured to obtain, when the third similarity degree is greater than the third threshold and less than the fourth threshold, a first to-be-tested gene subsequence unit and a second to-be-tested gene subsequence unit based on the second to-be-tested gene subsequence, wherein some bases of the first to-be-tested gene subsequence unit are the same as some bases of the second to-be-tested gene subsequence unit, and wherein the optical computing chip is further configured to:

input the first to-be-tested gene subsequence unit and the first reference gene subsequence;

perform a fifth optical alignment of the first to-be-tested gene subsequence unit and the first reference gene subsequence;

input the second to-be-tested gene subsequence unit and the first reference gene subsequence; and perform a sixth optical alignment of the second to-be-tested gene subsequence unit and the first reference gene subsequence.

10. The gene alignment apparatus of claim 7, wherein the processor is further configured to:

determine, based on the output result, that a first reference gene fragment of the reference gene fragments matches the to-be-tested gene sequence; and record a location of the first reference gene fragment in the reference gene sequence.

11. The gene alignment apparatus of claim 7, wherein the processor is further configured to separately perform optical encoding on the to-be-tested gene sequence and the reference gene fragments, and wherein the optical computing chip is further configured to separately input optical code of the to-be-tested gene sequence and optical code of the reference gene fragments.

12. The gene alignment apparatus of claim 7, wherein the processor is configured to further obtain the reference gene fragments from the gene database based on first m bases and last n bases of the to-be-tested gene sequence, wherein m and n are greater than 0, and wherein a sum of m and n is less than a quantity of bases in the to-be-tested gene sequence.

13. An alignment apparatus comprising:
a processor configured to:
  obtain a first group of reference objects from a database based on a first object, wherein at least some of the reference objects have some features that are the same as some features of the first object;
  determine, based on an output result of a first optical alignment, that a similarity degree between the first object and a first reference object in the reference objects is less than a first threshold and greater than a second threshold;
  obtain reference sub-objects based on a standard object, wherein each of the reference sub-objects is a part of one of the reference objects, and wherein the reference sub-objects comprise a first reference sub-object;
  make a determination that a first similarity degree is greater than a third threshold and less than a fourth threshold, wherein the fourth threshold is not greater than the first threshold; and
  obtain, in response to the determination, a first sub-object and a second sub-object based on the first object, wherein some data of the first sub-object is the same as some data of the second sub-object; and
an optical computing chip coupled to the processor and configured to:
  perform the first optical alignment between the first object and the reference objects;
  input the first object and the first reference sub-object;
  perform a second optical alignment of the first object and the first reference sub-object to obtain the first similarity degree between the first object and the first reference sub-object;
  input the first sub-object and the first reference sub-object;
  perform a third optical alignment between the first sub-object and the first reference sub-object to obtain a second similarity degree;
  input the second sub-object and the first reference sub-object; and
  perform a fourth optical alignment between the second sub-object and the first reference sub-object to obtain a third similarity degree.

14. The alignment apparatus of claim 13, wherein the processor is further configured to record, when the second similarity degree is greater than the fourth threshold, a location of the first reference sub-object in the standard object.

15. A non-transitory computer-readable storage medium comprising computer program instructions that, when executed by a processor, cause a gene alignment apparatus to:
  obtain reference gene fragments from a gene database based on a to-be-tested gene sequence, wherein the gene database comprises a reference gene sequence, wherein the reference gene sequence comprises the reference gene fragments, and wherein the reference gene fragments match some bases of the to-be-tested gene sequence;
  input the to-be-tested gene sequence and the reference gene fragments into an optical computing chip;
  perform a first optical alignment of the to-be-tested gene sequence and the reference gene fragments using the optical computing chip;
  determine, based on an output result of the first optical alignment, that a similarity degree between the to-be-tested gene sequence and a first gene fragment in the reference gene fragments is less than a first threshold and greater than a second threshold;
  obtain a plurality of reference gene subsequences from the reference gene sequence, wherein the reference gene subsequences comprise a first reference gene subsequence;
  input the to-be-tested gene sequence and the first reference gene subsequence into the optical computing chip;
  perform a second optical alignment of the to-be-tested gene sequence and the first reference gene subsequence to obtain a first similarity degree between the to-be-tested gene sequence and the first reference gene subsequence;
  make a determination that the first similarity degree is greater than a third threshold and less than a fourth threshold, wherein the fourth threshold is not greater than the first threshold;
  obtain, in response to the determination, a first to-be-tested gene subsequence and a second to-be-tested gene subsequence based on the to-be-tested gene sequence, wherein some bases of the first to-be-tested gene subsequence are the same as some bases of the second to-be-tested gene subsequence;
  input the first to-be-tested gene subsequence and the first reference gene subsequence into the optical computing chip;
  perform a third optical alignment of the first to-be-tested gene subsequence and the first reference gene subsequence to obtain a second similarity degree;
  input the second to-be-tested gene subsequence and the first reference gene subsequence into the optical computing chip; and
  perform a fourth optical alignment of the second to-be-tested gene subsequence and the first reference gene subsequence to obtain a third similarity degree.

16. The non-transitory computer-readable storage medium of claim 15, wherein the computer program instructions, when executed by the processor further cause the gene alignment apparatus to record, when the second similarity degree is greater than the fourth threshold, a location of the first reference gene subsequence in the reference gene sequence.

17. The non-transitory computer-readable storage medium of claim 15, wherein the computer program instructions, when executed by the processor further cause the gene alignment apparatus to:
  obtain, when the third similarity degree is greater than the third threshold and less than the fourth threshold, a first to-be-tested gene subsequence unit and a second to-be-tested gene subsequence unit based on the second to-be-tested gene subsequence, wherein some bases of the first to-be-tested gene subsequence unit are the same as some bases of the second to-be-tested gene subsequence unit;

input the first to-be-tested gene subsequence unit and the first reference gene subsequence;

perform a fifth optical alignment of the first to-be-tested gene subsequence unit and the first reference gene subsequence;

input the second to-be-tested gene subsequence unit and the first reference gene subsequence; and perform a sixth optical alignment of the second to-be-tested gene subsequence unit and the first reference gene subsequence.

18. The non-transitory computer-readable storage medium of claim 15, wherein the computer program instructions, when executed by the processor further cause the gene alignment apparatus to:

determine, based on the output result, that a first reference gene fragment of the reference gene fragments matches the to-be-tested gene sequence; and record a location of the first reference gene fragment in the reference gene sequence.

19. The non-transitory computer-readable storage medium of claim 15, wherein the computer program instructions, when executed by the processor further cause the gene alignment apparatus to separately perform optical encoding on the to-be-tested gene sequence and the reference gene fragments, and wherein the optical computing chip is further configured to separately input optical code of the to-be-tested gene sequence and optical code of the reference gene fragments.

20. The non-transitory computer-readable storage medium of claim 15, wherein the computer program instructions, when executed by the processor further cause the gene alignment apparatus to further obtain the reference gene fragments from the gene database based on first m bases and last n bases of the to-be-tested gene sequence, wherein m and n are greater than 0, and wherein a sum of m and n is less than a quantity of bases in the to-be-tested gene sequence.

21. An alignment method implemented by a computer system comprising an optical computing chip, the alignment method comprising:

obtaining a first group of reference objects from a database based on a first object, wherein at least some of the reference objects have some features that are the same as some features of the first object;

determining, based on an output result of a first optical alignment, that a similarity degree between the first object and a first reference object in the reference objects is less than a first threshold and greater than a second threshold;

obtaining reference sub-objects based on a standard object, wherein each of the reference sub-objects is a part of one of the reference objects, and wherein the reference sub-objects comprise a first reference sub-object;

making a determination that a first similarity degree between the first object and the first reference sub-object is greater than a third threshold and less than a fourth threshold, wherein the fourth threshold is not greater than the first threshold;

obtaining, in response to the determination, a first sub-object and a second sub-object based on the first object, wherein some data of the first sub-object is the same as some data of the second sub-object;

performing the first optical alignment between the first object and the reference objects;

inputting the first object and the first reference sub-object into the optical computing chip;

performing a second optical alignment of the first object and the first reference sub-object to obtain the first similarity degree;

inputting the first sub-object and the first reference sub-object into the optical computing chip;

performing a third optical alignment between the first sub-object and the first reference sub-object to obtain a second similarity degree;

inputting the second sub-object and the first reference sub-object into the optical computing chip; and performing a fourth optical alignment between the second sub-object and the first reference sub-object to obtain a third similarity degree.

22. The alignment method of claim 21, further comprising recording, when the second similarity degree is greater than the fourth threshold, a location of the first reference sub-object in the standard object.

* * * * *

SEQUENCE LISTING

<160> NUMBER OF SEQ ID NOS: 12

<210> SEQ ID NO 1
<211> LENGTH: 10
<212> TYPE: DNA
<213> ORGANISM: Unknown
<220> FEATURE:
<223> OTHER INFORMATION: Example sequence

<400> SEQUENCE: 1
aaaaaaaaaa                                                          10

<210> SEQ ID NO 2
<211> LENGTH: 10
<212> TYPE: DNA
<213> ORGANISM: Unknown
<220> FEATURE:
<223> OTHER INFORMATION: Example sequence -continued

<400> SEQUENCE: 2
aaaaaaaaac                                                                                  10

<210> SEQ ID NO 3
<211> LENGTH: 10
<212> TYPE: DNA
<213> ORGANISM: Unknown
<220> FEATURE:
<223> OTHER INFORMATION: Example sequence

<400> SEQUENCE: 3
aaaaaaaaag                                                                                  10

<210> SEQ ID NO 4
<211> LENGTH: 10
<212> TYPE: DNA
<213> ORGANISM: Unknown
<220> FEATURE:
<223> OTHER INFORMATION: Example sequence

<400> SEQUENCE: 4
aaaaaaaaat                                                                                  10

<210> SEQ ID NO 5
<211> LENGTH: 10
<212> TYPE: DNA
<213> ORGANISM: Unknown
<220> FEATURE:
<223> OTHER INFORMATION: Example sequence

<400> SEQUENCE: 5
aaaaaaaaca                                                                                  10

<210> SEQ ID NO 6
<211> LENGTH: 10
<212> TYPE: DNA
<213> ORGANISM: Unknown
<220> FEATURE:
<223> OTHER INFORMATION: Example sequence

<400> SEQUENCE: 6
aaaaaaaacc                                                                                  10

<210> SEQ ID NO 7
<211> LENGTH: 10
<212> TYPE: DNA
<213> ORGANISM: Unknown
<220> FEATURE:
<223> OTHER INFORMATION: Example sequence

<400> SEQUENCE: 7
aaaaaaaacg                                                                                  10

<210> SEQ ID NO 8
<211> LENGTH: 10
<212> TYPE: DNA
<213> ORGANISM: Unknown
<220> FEATURE:
<223> OTHER INFORMATION: Example sequence

<400> SEQUENCE: 8
aaaaaaaact                                                                                  10

<210> SEQ ID NO 9

-continued

```
<211> LENGTH: 10
<212> TYPE: DNA
<213> ORGANISM: Unknown
<220> FEATURE:
<223> OTHER INFORMATION: Example sequence

<400> SEQUENCE: 9
tttttaaaaa                                                    10

<210> SEQ ID NO 10
<211> LENGTH: 10
<212> TYPE: DNA
<213> ORGANISM: Unknown
<220> FEATURE:
<223> OTHER INFORMATION: Example sequence

<400> SEQUENCE: 10
tttttaaaac                                                    10

<210> SEQ ID NO 11
<211> LENGTH: 10
<212> TYPE: DNA
<213> ORGANISM: Unknown
<220> FEATURE:
<223> OTHER INFORMATION: Example sequence

<400> SEQUENCE: 11
tttttaaaat                                                    10

<210> SEQ ID NO 12
<211> LENGTH: 10
<212> TYPE: DNA
<213> ORGANISM: Unknown
<220> FEATURE:
<223> OTHER INFORMATION: Example sequence

<400> SEQUENCE: 12
tttttttttt                                                    10
```